United States Patent [19]

Hagishita et al.

[11] Patent Number: 4,904,819
[45] Date of Patent: Feb. 27, 1990

[54] BICYCLIC SULFONAMIDE DERIVATIVES AND PROCESS THEREFOR

[75] Inventors: Sanji Hagishita, Nara; Kaoru Seno, Hyogo, both of Japan

[73] Assignee: Shionogi & Co., Ltd., Osaka, Japan

[21] Appl. No.: 187,645

[22] Filed: Apr. 28, 1988

[30] Foreign Application Priority Data

May 8, 1987 [JP] Japan .................. 62-113086

[51] Int. Cl.$^4$ .............................. C07C 69/74
[52] U.S. Cl. ..................... 560/118; 560/12; 560/138; 562/427
[58] Field of Search ............ 560/118, 12, 138; 562/427

[56] References Cited

U.S. PATENT DOCUMENTS 3,449,346  6/1969  Aumüller ............... 562/427
3,706,790  12/1972  Sprague et al. ......... 562/427
3,806,534  4/1974  Feit et al. ............. 562/427
3,992,440  11/1978  Werner ................. 562/427
4,389,413  6/1983  Homanka ............... 562/427
4,443,477  4/1984  Witte et al. ........... 562/427

Primary Examiner—Paul J. Killos
Attorney, Agent, or Firm—Wenderoth, Lind & Ponack

[57] ABSTRACT

Bicyclic sulfonamide derivatives represented by the formula:

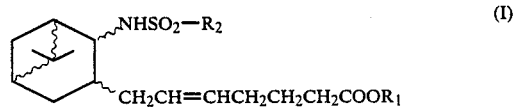

(wherein $R_1$ is hydrogen or lower alkyl; $R_2$ is lower alkyl, aralkyl, or aryl which may be substituted by lower alkyl, alkoxy, acetoxy, hydroxy, halogen, nitro or phenyl; and the wavy line indicates R or S configuration or their mixture) or their salt being used as antithrombotic, antivasoconstricting, and antibronchoconstricting drugs and the process therefor.

8 Claims, No Drawings

BICYCLIC SULFONAMIDE DERIVATIVES AND PROCESS THEREFOR

BACKGROUND OF THE INVENTION (1) Field of the Invention

The present invention relates to new compounds used as medicines for improving symptoms caused by thromboxane and the process therefor. In more detail, this invention relates to novel pinane type sulfonamide derivatives to which unsaturated fatty acid is attached and the process therefor. The compounds of the present invention are used as antithrombotic, anti-vasoconstricting, and anti-bronchoconstricting drugs.

(2) Prior Art

The general course of atherosclerosis, which is regarded as the main risk factor of myocardial infarction and cerebral infarction, begins in the arterial intima with mucoid accumulation and fibroblast formation, progressively followed by degeneration, deposition of lipid and cholesterol and destruction and atheromasia of the intima tissue, with gradual formation of high-degree and localized hypertrophy in the intima. The atherosclerosis has long been regarded to be caused by thrombuse formation and fibrin deposition, but recent discoveries of thromboxane $A_2$ ($TXA_2$) by Samuelsson et al. and prostacycline ($PGI_2$) by Vane et al. have revealed an interaction between platelets and vessel wall. Platelets are said to play an important role in the onset and progress of atherosclerosis. Therefore, it is now recognized that the use of antithrombotic drugs, particularly drugs which inhibits platelet aggregration, are effective for the treatment of atherosclerotic diseases.

In addition to the conventional antithrombotic drugs such as heparin and coumarin compounds, certain types of prostaglandins are known to have a potent platelet aggregation inhibitory action. From these facts, prostaglandin derivatives have attracted much attention as possible antithrombotic drugs. For example, analogues of prostaglandin $E_1$ and $I_2$ receptor agonists have been developed. Since thromboxane $A_2$ shows potent platelet aggregation and vasoconstriction action, thromboxane $A_2$ synthesis inhibitors, such as cyclooxygenase inhibitors and thromboxane synthetase inhibitors, and thromboxane $A_2$ receptor antagonists, have been developed. The thromboxane $A_2$ receptor antagonists include 13-APA (Venton D. L. et al., J. Med. Chem., 22, 824 (1979)), $PTA_2$ (Lefer A. M. et al., Proc. Natl. Acad. Sci. U.S.A., 76, 2566, (1979)), BM-13177 (Lefer A. M. et al., Drugs of Today, 21, 283 (1985)), SQ-29548 (Ogletree et al., J. Pharmacol. Exp. Ther., 34, 435, (1985)) or the like. The thromboxane $A_2$ receptor antagonists are also disclosed in Japan Kokai No. 83-13551, Japan Kokai No. 86-49, USP 4,654,357 or the like.

When thrombin acts on platelets, cyclooxygenase is activated. By activation of cyclooxygenase, thromboxane $A_2$ is produced enzymatically in platelets, vessel wall, and various other cells, from arachidonic acid through prostaglandins $G_2$ and $H_2$. This product has various potent physiologic or pathogenic actions. In particular, the potent platelet aggregation action and the action constricting the smooth muscle of bronchi, and of coronary, cerebral and pulmonary arteries, etc. are considered to be the factors which relate to the onset and progress of such circulatory and respiratory diseases as angina pectoris, myocardial infarction, cerebral infarction, and bronchial asthma. Moreover, it is said that the strong action occures even at a concentration of $10^{-10}$ to $10^{-11}M$. Therefore, increasing attention has been paid to the development of thromboxane $A_2$ antagonists or inhibitors as anti-thrombotics, anti-vasoconstrictives or anti-bronchoconstrictives. Inhibitors, however, have some problems in view of that they influence on prostaglandins which bear various important roles other than thromboxane $A_2$ and uncontrollable thromboxane-like harmful effects are caused by accumulated substrates such as prostaglandins $H_2$. So, development of antagonists has especially been sought.

SUMMARY

Bicyclic sulfonamide derivatives represented by the formula:

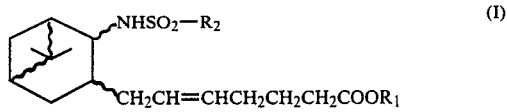

(wherein $R_1$ is hydrogen or lower alkyl; $R_2$ is lower alkyl, aralkyl, or aryl which may be substituted by lower alkyl, alkoxy, acetoxy, hydroxy, halogen, nitro or phenyl; and the wavy line indicates R or S configuration, or their mixture) or their salts and the process therefor are provided in this invention. Said compounds are used as antithrombotic, antivasoconstricting and antibronchoconstricting drugs.

DESCRIPTION OF THE PREFERRED EMBODIMENTS

The inventors succeeded in the synthesis of the bicyclic sulfonamide derivatives represented by the general formula (I) and the salts thereof and found that these new compounds have potent activity as thromboxane $A_2$ receptor antagonists, and are chemically and biochemically stable. The present invention was based on these findings.

General formula:

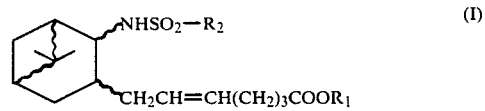

(wherein $R_1$ is hydrogen or lower alkyl; $R_2$ is lower alkyl, aralkyl, or aryl which may be substituted by lower alkyl, alkoxy, acetoxy, hydroxy, halogen, nitro or phenyl; and the wavy line indicates R or S configuration, or their mixture).

The compounds of the present invention can be prepared by the following processes A and B.

PROCESS A

A process for preparing a compound of the formula:

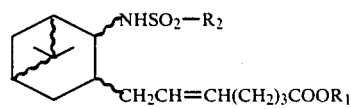

(wherein $R_1$ is hydrogen or lower alkyl; $R_2$ is lower alkyl, aralkyl, or aryl which may be substituted by lower alkyl, alkoxy, acetoxy, hydroxy, halogen, nitro or phenyl; and the wavy line indicates R or S configuration, or their mixture) or salt thereof which comprises reacting a compound of the formula:

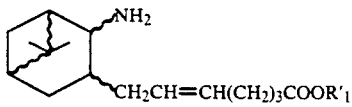

(wherein $R'_1$ is lower alkyl; and the wavy line is the same defined above) or salt thereof with a compound of the formula: Hal—$SO_2$—$R_2$ (wherein Hal is halogen; and $R_2$ is the same as defined above) and, if necessary, applying the resulting compound to hydrolysis and/or salt formation.

PROCESS B

A process for preparing a compound of the formula:

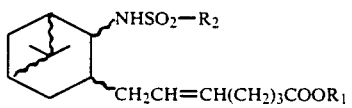

(wherein $R_1$ is hydrogen or lower alkyl; $R_2$ is lower alkyl, aralkyl, or aryl which may be substituted by lower alkyl, alkoxy, acetoxy, hydroxy, halogen, nitro or phenyl; and the wavy line indicates R or S configuration, or their mixture) or salt thereof which comprises reacting a compound of the formula:

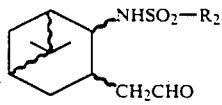

(wherein $R_2$ and the wavy line each is the same as defined above) or its equivalent with a compound of the formula:

$$(Ar)_3P=CH-(CH_2)_3COOR_1$$

(wherein Ar is aryl; and $R_1$ is the same as defined above) and, if necessary, applying the resulting compound to esterfication, hydrolysis and/or salt formation.

The following definitions are given for various terms used throughout this specification.

The term "lower alkyl" refers to both straight and branched $C_1$–$C_5$ alkyl, e.g., methyl, ethyl, n-propyl, isopropyl, butyl, tert-butyl, pentyl or the like.

The term "alkoxy" refers to $C_1$–$C_5$ alkoxy, e.g., methoxy, ethoxy, propoxy, isopropoxy, butoxy, tert-butoxy or the like.

The term "aryl" refers phenyl, naphthyl, poly aromatic hydrocarbon or the like.

The term "aralkyl" refers to lower alkyl substituted by aryl, e.g., benzyl, phenethyl, 3-phenylpropyl, 4-phenylbutyl, 5-phenylpropyl or the like.

The term "aryl" which represented by "Ar" refers to phenyl or substituted phenyl, e.g., tolyl, methoxyphenyl or the like.

The term "halogen" refers to fluorine, chlorine, bromine, or iodine.

The term "equivalent" means tautomer.

In general formula, preferable $R_1$ is hydrogen or lower alkyl, e.g., methyl, ethyl, propyl, isopropyl, butyl, tert-butyl, pentyl or the like. Preferable $R'_1$ is lower alkyl, e.g., methyl, ethyl, propyl, isopropyl, butyl, tert-butyl, pentyl or the like. Preferable $R_2$ is lower alkyl, aralkyl, e.g., methyl, ethyl, propyl, isopropyl, butyl, tert-butyl, pentyl or benzyl, phenethyl, 3-phenylpropyl, 4-phenylbutyl, 5-phenylpentyl or the like, or aryl which may be substituted by lower alkyl, alkoxy, acetoxy, hydroxy, halogen, nitro or phenyl, e.g., phenyl, naphthyl, 4-tolyl, 4-ethylphenyl, 4-propylphenyl, 4-isopropylphenyl, 4-tert-butylphenyl, 2-methoxyphenyl, 4-methoxyphenyl, 4-ethyoxyphenyl, 4-propoxyphenyl, 4-acetoxyphenyl, 4-hydroxyphenyl, 2-chlorophenyl, 3-chlorophenyl, 4-chlorophenyl, 2-fluorophenyl, 3-fluorophenyl, 4-fluorophenyl, 2-nitrophenyl, 4-nitrophenyl or the like. Preferable Hal is halogen, e.g., chlorine, bromine or iodine. Preferable Ar is phenyl or substituted phenyl, e.g., tolyl, methoxyphenyl or the like.

Especially $R_1$ is hydrogen or lower alkyl, e.g., methyl. Especially $R'_1$ is lower alkyl, e.g., methyl. Especially $R_2$ is lower alkyl, aralkyl, e.g., methyl, benzyl, phenethyl, 3-phenylpropyl or the like, or aryl which may be substituted by lower alkyl, alkoxyl, acetoxy, hydroxy, halogen, nitro or phenyl, e.g., phenyl, naphthyl, 4-tolyl, 4-ethylphenyl, 2-methoxyphenyl, 4-methoxyphenyl, 4-acetoxyphenyl, 4-hydroxyphenyl, 2-chlorophenyl, 3-chlorophenyl, 4-chlorophenyl, 4-fluorophenyl, 4-nitrophenyl or the like. Especially Hal is halogen, e.g., chlorine or the like. Especially Ar is phenyl or substituted phenyl, e.g., tolyl or the like.

The salts of amine include, for example, salt with trifluoroacetic acid or the like.

The salts of the compound represented by the general formula (I) include, for example, salts with alkaline metal such as lithium, sodium, and pottassium, salts with alkaline earth metal such as calcium, ammonium salts, salts with organic base such as triethylamine, 2-aminobutane, tert-butylamine, diisopropylethylamine, n-butylmethylamine, n-butyldimethylamine, tri-n-butylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthlenemethylamine, diphenylamine, triphenylamine, 1-naphthylamine, 1-aminoanthracene, 2-aminoanthracene, dehydroabietylamine, N-methylmorpholine, pyridine, and salts with amino acid such as lysine and arginine.

Illustrative of the compounds of the present invention are as follows.

7-(6,6-Dimethyl-2-methanesulfonamidobicyclo[3.1.1-]hept-3-yl)-5-heptenoic acid, 7-(6,6-dimethyl-2-phenylmethanesulfonamidobicyclo[3.1.1]hept-3-yl)-5-heptenoic acid, 7-[6,6-dimethyl-2-(2-phenylethanesulfonamido)-bicyclo[3.1.1]hept-3-yl]-5-heptenoic acid, 7-[6,6-dimethyl-2-(3-phenylpropanesulfonamido)-bicyclo[3.1.1]hept-3-yl]-5-heptenoic acid, 7-[2-(2-chlorobenzenesulfonamide)-6,6-dimethyl-bicyclo[3.1.1]hept-3-yl]-5-heptenoic acid, 7-[2-(3-chlorobenzenesulfonamido)-6,6-dimethyl-bicyclo[3.1.1]hept-3-yl]-5-heptenoic acid, 7-[2-(4-chlorobenzenesulfonamido)-6,6-dimethyl-bicyclo[3.1.1]hept-3-yl]-5-heptenoic acid, 7-[6,6-dimethyl-2-(4-fluorobenzenesulfonamido)-bicyclo[3.1.1]hept-3-yl]-5-heptenoic acid, 7-[6,6-dimethyl-2-(4-ethylbenzenesulfonamido)-bicyclo[3.1.1]hept-3-yl]-5-heptenoic acid,
7-[6,6-dimethyl-2-(4-nitrobenzenesulfonamido)-bicyclo[3.1.1]hept-3-yl]-5-heptenoic acid,
7-[6,6-dimethyl-2-(4-methoxybenzenesulfonamido)-bicyclo[3.1.1]hept-3-yl]-5-heptenoic acid,
7-[2-(4-acetoxybenzenesulfonamido)-6,6-dimethyl-bicyclo[3.1.1]hept-3-yl]-5-heptenoic acid,
7-[6,6-dimethyl-2-(4-hydroxybenzenesulfonamido)-bicyclo[3.1.1]hept-3-yl]-5-heptenoic acid,
7-[6,6-dimethyl-2-(4-toluenesulfonamido)bicyclo[3.1.1]hept-3-yl]-5-heptenoic acid,
7-[2-(4-biphenylsulfonamido)-6,6-dimethylbicyclo[3.1.1]hept-3-yl]-5-heptenoic acid,
7-[6,6-dimethyl-2-(2-naphthalenesulfonamido)-bicyclo[3.1.1]hept-3-yl]-5-heptenoic acid, and their carboxylate esters and salts.

The compounds of the present invention represented by the general formula (I) include all of the possible stereoisomeric forms (e.g., diastereomer, epimer, enantiomer or the like).

Among all of the stereoisomers which are included in the compounds of the present invention (I), the 5(E) and 5(Z) isomers can be shown by the following formulae. (In the following formulae, only one enantiomer is shown.)

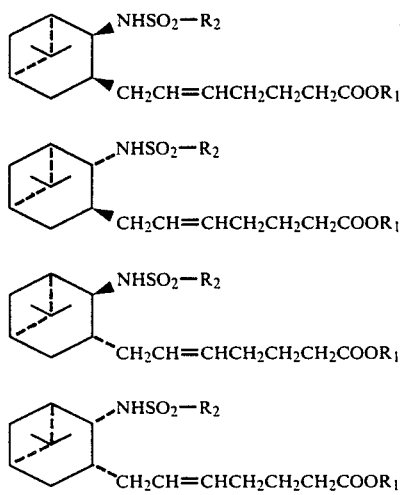

(wherein $R_1$ and $R_2$ each has the same meaning as defined above.)

The starting material for the processes A and B can be prepared in the following reaction sequence, in which details of the processes A and B are given.

Process scheme-1 (Preparation of Ia, Ib, Ic or Ie)

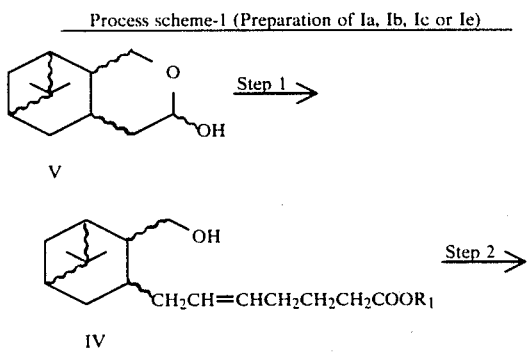

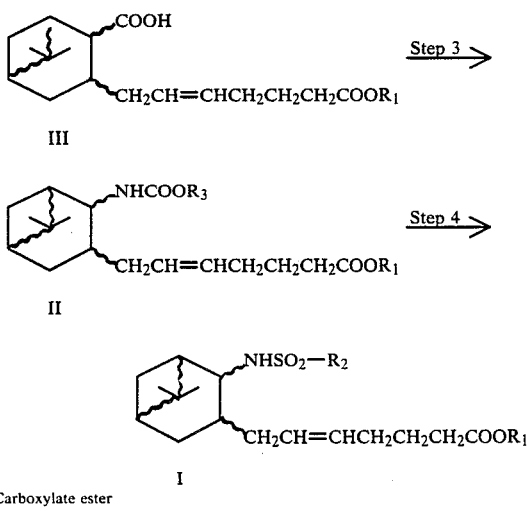

I-a Carboxylate ester
I-b Free carboxylic acid
I-c Carboxylate salt

PROCESS-1 (Preparation of Ia, Ib, Ic or Ie)

(Step 1)

In this step, the aldehyde equivalent V is allowed to react with an ylide in accordance to the Wittig reaction to give the compound IV. The ylide used is prepared by base treatment of the phosphonium salt which has been prepared from a 5-halogenopentanoic acid by reaction with triphenylphosphine. For the base treatment, sodium dimsyl, potassium dimsyl, potassium tert-butoxide, sodium hydride, n-butyl lithium or lithium diisopropylamide is exemplified as a base. As the 5-halogenopentanoic acid, 5-chloropentanoic acid, 5-bromopentanoic acid or the like is exemplified. This step can be carried out in a solvent such as an ether, (e.g., ethyl ether, tetrahydrofuran), n-hexane or dimethylsulfoxide at a temperature of $-10°$ C. to room temperature for several hours.

To protect from the subsequent reaction, the carboxy of the 3-side chain, for example, may be esterified. The esterification may be effected by one of the following conventional methods: a method for reacting the carboxylic acid with an alcohol such as methanol, ethanol, n-propanol, isopropanol, butanol or pentanol in the presence of a catalyst, as required, such as dry hydrogen chloride or concentrated sulfuric acid; a method for reacting a halogenide prepared from the carboxylic acid with an alcohol as cited above in the presence of a base such as N,N-dimethylaniline, pyridine, or sodium hydroxide; a method employing a metal alkoxide; a method employing diazomethane; and a method employing dimethyl sulfuric acid and diazabicyclononene or diazabicycloundecene.

In this step of the Wittig reaction, the Z-form alone or a mixture of the Z-form and E-form is produced in a certain reaction condition.

(Step 2)

In this step, the hydroxy of the compound IV is oxidized to give the compound III.

This step can be carried out by oxidizing the hydroxy into the carboxy directly or through an aldehyde.

As an oxidizing agent, a chromate-type agent such as Jones' reagent, Collins' reagent, pyridinium chlorochromate or pyridimium dichromate, or dimethylsulfoxide combined with sulfur trioxide, trifluoroacetic anhydride, methanesulfonic anhydride, thionyl chloride or oxalyl chloride or the like may be used. In a case where dimethylsulfoxide is used as an oxidizing agent, a tertiary amine, e.g., triethylamine or pyridine may be used as a decomposing agent. As a solvent, chlorinated hydrocarbon such as chloroform or dichloromethane, ether such as diethyl ether or tetrahydrofuran, or dimethylformamide or acetone may be used depending on the property of the agent used. The reaction may be carried out under cooling or at room temperature for several hours.

(Step 3)

In this step, the 2-carboxy group of the compound III is converted into the acid azide, which is then rearranged into the isocyanate, which is then allowed to react with an alcohol to yield the urethane II. This step can be achieved by the Curtius rearrangement; that is, the acid azide compound is prepared by the reaction of sodium azide with either of the acid chloride or active ester of the compound III; the acid chloride is prepared by treating the carboxy group with thionyl chloride, phosphoryl chloride, or phosphorus pentachloride; the active ester is prepared by allowing the carboxy group to react with ethyl chloroformate or isobutoxycarbonyl chloride in the presence of a basic catalyst such as triethylamine or 4-dimethylaminopyridine in a solvent such as acetone, dimethylformamide, dimethylsulfoxide, ethyl acetate, or tetrahydrofuran for several tens of minutes to several hours under cooling. The isocyanate can be prepared by refluxing the acid azide compound in benzene, toluene, or diphenyl ether for several tens of minutes to several hours. The alcohol which reacts with the isocyanate includes those giving an urethane which might readily yield the desired primary amine, for example, isobutanol, tert-butanol, diisopropylmethanol, cyclopentanol, cyclohexanol, benzyl alcohol, diphenylmethanol or triphenylmethanol. This reaction can be achieved by several hours reflux in a solvent such as aromatic solvent, e.g., benzene, chlorinated hydrocarbon, (e.g., dichloromethane, chloroform), ethyl acetate, acetone or the like in the presence of a base such as triethylamine, 4-dimethylaminopyridine, or 4-pyrrolidinopyridine, as required.

(Step 4)

In this step, the compound II is allowed to react in the following manner to give the compound I of the present invention.

The removal of the amino protecting group is achieved by a conventional method, for example, hydrolysis with an acid such as hydrochloric acid or sulfuric acid or a base such as sodium hydroxide, potassium hydroxide or barium hydroxide, decarboxylation with trifluoroacetic acid, hydrogenolysis, or the like. The product can be used in the form of ammonium salt in the subsequent step, and if necessary, it may be converted into the free amine by the treatment with an adequate base such as sodium carbonate or sodium hydrogencarbonate.

The subsequent reaction to give the sulfonamide derivatives is achieved with a substituted sulfonyl halide which has a desired substituent, such as lower alkyl sulfonyl halide (e.g., methanesulfonyl chloride, methanesulfonyl bromide, ethanesulfonyl chloride, ethanesulfonyl bromide, propanesulfonyl chloride, isopropanesulfonyl chloride, butanesulfonyl chloride, butanesulfonyl bromide, tert-butanesulfonyl chloride or the like), aralkyl sulfonyl halide (e.g., benzenesulfonyl chloride, phenethylsulfonyl chloride, 3-phenylpropanesulfonyl chloride or the like), aryl sulfonyl halide (e.g., benzenesulfonyl chloride, benzenesulfonyl bromide, naphthylsulfonyl chloride, naphthylsulfonyl bromide or the like) or substituted aryl sulfonyl halide (e.g., 4-tolyl chloride, 4-tolyl bromide, 4-ethylbenzenesulfonyl chloride, 4-biphenylsulfonyl chloride, 4-nitrobenzenesulfonyl chloride, 4-methoxybenzenesulfonyl chloride, 4-fluorobenzenesulfonyl chloride, 4-fluorobenzenesulfonyl bromide, 4-acetoxybenzenesulfonyl chloride) in the presence of a base such as pyridine or triethylamine in a solvent such as chlorinated hydrocarbon, e.g., chloroform or dichloromethane, ether, e.g., ethyl ether or tetrahydrofuran, or aromatic hydrocarbon, e.g., benzene, at room temperature for several tens of minutes. In this reaction, the carboxylic acid ester I-a which is a compound of the present invention is prepared.

The carboxylic acid ester I-a is converted into the free carboxylic acid I-b, a compound of the present invention, in a conventional manner for hydrolysis of esters (another ester function if any is also hydrolyzed.) In carrying out the hydrolysis, a catalyst such as hydrochloric acid, sulfuric acid, sodium hydroxide, potassium hydroxide or barium hydroxide is used. As a solvent, methanol-water, ethanol-water, acetone-water, or acetonitrile-water is used. If necessary, the free carboxylic acid I-b is converted into a salt of the carboxylic acid I-c, a compound of the present invention represented by the general formula (I), by treating in the conventional manner using base such as sodium methoxide, sodium hydroxide, potassium hydroxide, calcium hydroxide, ammonium hydroxide, dicyclohexylamine, methylmorpholine, pyridine, triethylamine, lysine or arginine.

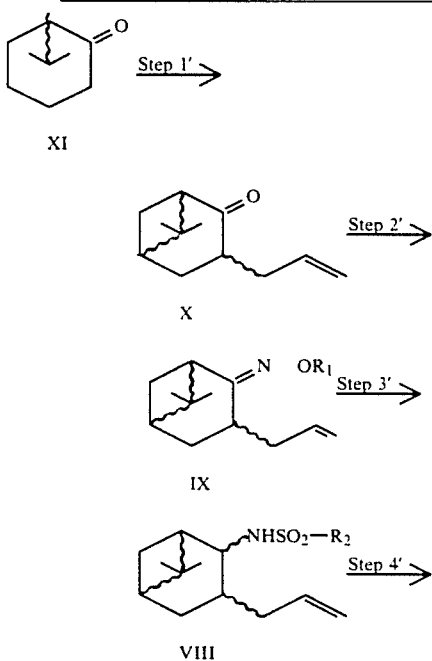

Process scheme-2 (Preparation of Ib, Ic or Id)

-continued
Process scheme-2 (Preparation of Ib, Ic or Id)

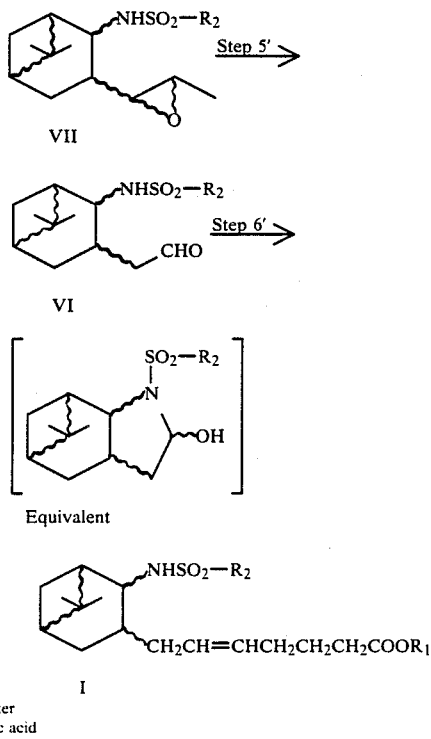

Equivalent

I-a Carboxylate ester
I-b Free carboxylic acid
I-c Carboxylate salt

PROCESS-2 (Preparation of Ib, Ic or Id)

Step 1')

In this step, an allyl group is introduced into the active methylene of the compound XI. As an allylation agent, allyl halide such as allyl chloride, allyl bromide, or allyl iodide is used. As a catalyst, a relatively strong base such as sodium amide, potassium tert-butoxide, sodium hydride or lithium diisopropylamide is used. As a solvent, it is desirable to use an ether such as tetrahydrofuran, ethyl ether, glyme or diglyme.

The reaction is carried out at a temperature of $-78°$ C. to 25° C. for a period of several minutes to several hours.

In this step, a diallyl-product sometimes may also be produced.

(Step 2')

In this step, the ketone of the compound X is converted into an oxime. The oxime formation may be carried out using hydroxylamine hydrochloride or O-methylhydroxylamine hydrochloride in the presence of a base. As a base, pyridine, potassium hydroxide, sodium carbonate, sodium acetate or the like is used and as a solvent, an alcohol, e.g., methanol, ethanol or the like, or water is used singly or as a mixture. The reaction is carried out at room temperature or under heating for a period of several tens of minutes to several tens of hours.

(Step 3')

In this step, the oxime of the compound IX is reduced to an amine, which is then allowed to react with a substituted sulfonyl halide without purification to give a compound VIII.

The reduction is effected with sodium metal, zinchydrochloric acid, stannous chloride-hydrochloric acid, sodium-alcohol, lithium aluminium hydride or the like. As a solvent, an ether, e.g., ethyl ether, tetrahydrofuran, diglyme or the like, or alcohol, e.g., ethanol, methanol or the like is used in this reduction. The reaction is carried out at room temperature or under refluxing for several hours. The reaction of the amine to the compound VIII may be carried out in the same manner as in Step 4.

(Step 4')

In this step, the double bond of the compound VIII is oxidized to form an epoxide to give a compound VII.

As an oxidizing agent, a combined reagent of hydrogen peroxide with a transition metal catalyst or a peroxy acid or its ester such as performic acid, peracetic acid, perbenzoic acid, monoperphthalic acid, monopermaleic acid, pertrifluoroacetic acid, metachloroperbenzoic acid or paranitroperbenzoic acid may be used. As a solvent, an ether, e.g., ethyl ether, tetrahydrofuran, or the like, alcohol, e.g., methanol, ethanol or the like, or chlorinated hydrocarbon, e.g., dichloromethane, chloroform or the like is exemplified. The reaction is carried out at a temperature of 0° C. to room temperature for a period of several minutes to several hours. The epoxide prepared in this step may be a mixture of epimers.

(Step 5')

In this step, the epoxide VII is converted into an aldehyde VI losing one carbon through oxidative cleavage of the glycol produced by hydration. As an oxidizing agent which also serve as a hydrating catalyst, periodic acid or orthoperiodic acid may be used. It is desirable to use a solvent which is miscible with water, such as an ether, e.g., ethyl ether, tetrahydrofuran, dioxane or the like, or alcohol, e.g., methanol, ethanol or the like. The reaction is carried out at room temperature for a period of several tens of minutes to several hours.

The compound VIII can be converted into the compound VI in one step by ozonolysis which attains simultaneously the reactions of Steps 4' and 5'.

(Step 6')

In this step, the aldehyde VI or its cyclic equivalent is allowed to react with an ylide to give the compound (I) of the present invention. This step may be carried out in accordance with Step 1. The prepared carboxylate I-a or free carboxylic acid I-b, the compound of present invention, is converted into a salt of the carboxylic acid I-c by treatment in accordance with Step 4.

In the process scheme, $R_1$ and $R_2$ each has the same meaning as defined above. $R_3$ is a carboxy protecting group ordinarily used, for example, alkyl (e.g., diisopropylmethyl, isobutyl, tert-butyl or the like), cycloalkyl (e.g., cyclopentyl or the like), aryl (e.g., benzyl or the like) or aralkyl (e.g., diphenylmethyl or the like).

The wavy line indicates R or S configuration or their mixture.

The salts of the compounds of the general formula (I) are the same as mentioned above.

Each starting compound of the present invention can be prepared in the method described in Helv. Chim. Acta., 66, 989 (1983) or J. Org. Chem., 50, 1904, (1985).

The following examples and physical constants are included to explain the embodiment of the present invention in more detail, but these are not intended to limit the scope of the invention.

PREPARATION OF INTERMEDIATE 1-(1) Methyl (−)-5(Z)-7-[(1S, 2S, 3S, 5S)-2-hydroxymethyl-6,6-dimethylbicyclo[3.1.1]hept-3-yl]-5-heptenoate 2a

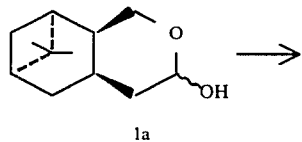

1a

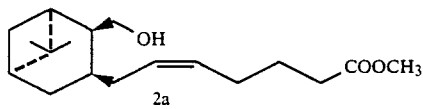

2a

A mixture of 4 g of 60% sodium hydride dispersed in mineral oil and 100 ml of dimethylsulfoxide is stirred at 80° C. in atmosphere of nitrogen for about 1 hour until the generation of hydrogen gas ceases. After cooling to room temperature, a solution of 22.15 g of (4-carboxybutyl)triphenylphosphonium bromide in 60 ml of dimethylsulfoxide is added and the mixture is stirred for 15 minutes. To the above mixture is added a solution of 3.73 g of (−)-(4aR, 6S, 8S, 8aS)-7,7-dimethyl-6,8-methaneperhydroisochroman-3-ol 1a in 50 ml of dimethylsulfoxide and the mixture is stirred at room temperature for 2.5 hours. The reaction mixture to which is added 300 ml of ice-chilled water is extracted with 200 ml of ether. The aqueous layer which is adjusted to about pH 3 with 10% hydrochloric acid is extracted with 300 ml of ether and the ether layer is washed with water. To the ether extract cooled with ice-water is added an excess amount of a diazomethane ether solution and the mixture is stirred for 10 minutes. The reaction mixture is evaporated and the residue is purified by frash column chromatography (240 g of silica gel, 230-400 mesh, eluted with hexane-ethyl acetate=4:1 to 2:1) to give 4.01 g of the titled compound 2a as an oil in 71.7% yield.

[α]$_D$: −3.5° (23° C., c 1.060, CH$_3$OH).

IR ν max(film): 3430, 1740 cm$^{-1}$.

NMR δ ppm(CDCl$_3$): 0.87(3H,s), 1.11(1H,d,J=9Hz), 1.20(3H,s), 1.32-2.70(16H), 3.55(1H,dd,J=6,10 Hz), 3.54(1H,dd,J=6,10 Hz), 3.66(3H,s), 3.86(1H,dd,J=6,10 Hz), 5.27(2H,m).

Anal. Calcd. (%) for C$_{18}$H$_{30}$O$_O$: C 73.43, H 10.27. Found (%): C 73.17, H 10.06.

(2) Methyl (+)-5(Z)-7-[(1S, 2S, 3S, 5S)-2-hydroxymethyl-6,6-dimethylbicyclo[3.1.1]hept-3-yl]-5-heptenoate 2b

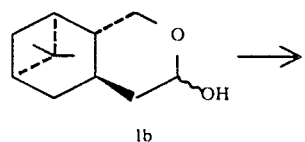

1b

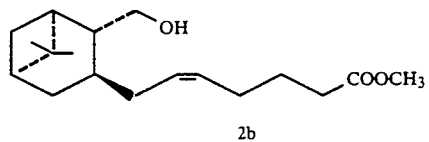

2b

Compound 1b is allowed to react in the same manner as in 1-(1) to give compond 2b
Yield 91.7%
[α]$_D$ +34.1° (23° C., c 1.309, CH$_3$OH).
IR ν max(film): 3440, 1742 cm$^{-1}$.
NMR δ ppm(CDCl$_3$): 0.85(1H,d,J=9 Hz), 0.94(3H,s), 1.19(3H,s), 1.35∼2.5 (16H), 3.57(2H,d,J=7 Hz), 3.65 (3H,s,), 5.43(2H,m).

Anal. Calcd. (%) for C$_{18}$H$_{30}$O$_O$: C 73.43, H 10.27. Found (%): C 73.22, H 10.38.

(3) Methyl (−)-5(Z)-7-[(1R, 2S, 3R, 5R)-2-hydroxymethyl-6,6-dimethylbicyclo[3.1.1]hept-3-yl]-5-heptenoate 2e

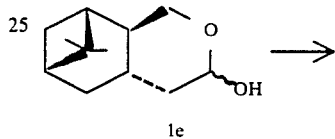

1e

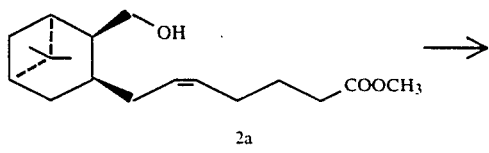

2e

Compound 1e is allowed to react in the same manner as in 1-(1) to give compound 2e.
Yield 75.6%.
[α]$_D$−32.3° 23° C., c 1.042, CH$_3$OH).

IR and NMR data of compound 2e are identical with those of compound 2b [prepared in 1-(2)].

PREPARATION OF INTERMEDIATE 2-(1) Methyl 5(Z)-7-[(1S, 2S, 3S, 5S)-2-carboxy-6,6-dimethylbicyclo[3.1.1]hept-3-yl]-5-heptenoate 3a

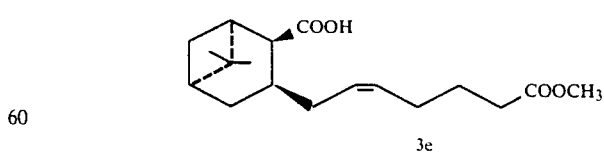

To a solution of 2.10 g of alcohol 2a [prepared in 1-(1)] in 20 ml of acetone is dropwise added 3.8 ml of 3M Jones' reagent at 0° C. under stirring and the mixture is stirred at 0° C. for 1 hour. Water is added to the reaction mixture to dissolve solid material and the mixture is extracted with ether. The extract is washed well with water, dried over anhydrous sodium sulfate and evaporated under reduced pressure to give 2.12 g of the titled compound 3a, which is used in the next reaction without further purification, in 96.6% yield.

IR Γ max(film): 1740, 1706 cm⁻¹.

NMR δ ppm(CDCl₃): 0.90(3H,s), 1.22(3H,s), 1.4~2.7(15H), 3.18(1H,m), 3.65(3H,s), 5.35(2H,m), 8.95(1H,br.s).

(2) Compound 2b [prepared in 1-(2)] is allowed to react in the same manner as in 2-(1) to give compound 3b

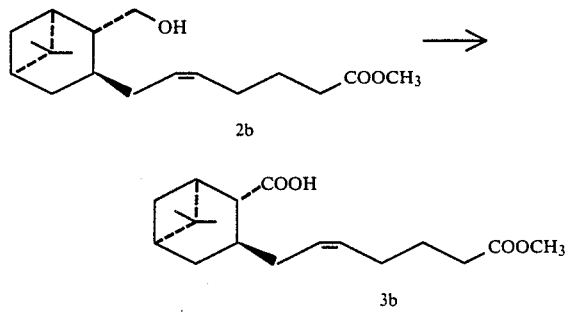

Yield 93.4%.

IR ν max(film): 1740, 1700 cm⁻¹.

NMR δ ppm(CDCl₃): 0.88(3H,s), 0.94(1H,d,J=10 Hz), 1.20(3H,s), 1.4~2.9 (15H), 3.64(3H,s), 5.43(2H,m), 9.70(1H,br.s).

(3) Compound 2e [prepared in 1-(3)] in the same manner as in 2-(1) to give compound 3e Yield 97.7%.

IR and NMR data are identical with those of compound 3b.

(4) Methyl 5(Z)-7-[(1S, 2S, 3R, 5S)-2-carboxy-6,6-dimethylbicyclo[3.1.1]hept-3-yl]-5-heptenoate 3c

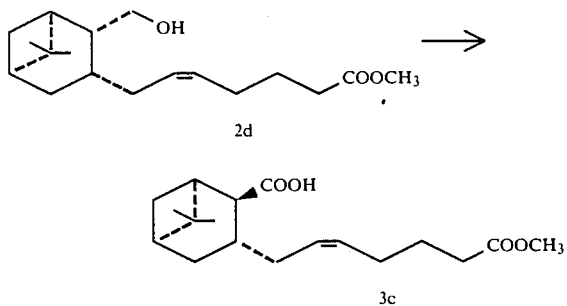

To a solution of 1.0 ml of oxalyl chloride in 25 ml of dichloromethane are dropwise added a solution of 1.7 ml of dimethylsulfoxide in 15 ml of dichloromethane at −60° C. under stirring and then a solution of 3.0 g of alcohol 2d in 30 ml of dichloromethane at the same temperature and the mixture is stirred for 1 hour. A solution of 9 ml of triethylamine in 15 ml of dichloromethane is added thereto and the mixture is slowly warmed up to room temperature. The reaction mixture is poured into water and the organic layer is separated. The aqueous layer is extracted with dichloromethane. The combined organic layers are washed with water, dried over anhydrous sodium sulfate and evaporated under reduced pressure to give the corresponding 2α,-3α-aldehyde.

This crude aldehyde is dissolved in 40 ml of 0.375M solution of sodium methoxide in methanol and the mixture is allowed to stand at room temperature for 1 hour. The mixture is acidified with dilute hydrochloric acid and extracted with dichloromethane. The extract is washed with water, dried over anhydrous sodium sulfate and evaporated under reduced pressure to give the trans-aldehyde, which is oxidized with Jones' reagent in the same manner as in 2-(1).

The prepared crude carboxylic acid 3c is purified by frash column chromatography on silica gel.

Yield 70.1%

[α]_D−47.4° (20° C., c 1.474, CH₃OH).

IR ν max(film): 1741, 1702 cm⁻¹.

NMR δ ppm(CDCl₃): 0.82 (3H,s), 1.22(3H,s), 1.4~2.2(16H), 3.67(3H,s), 5.43(2H,m), 9.73(1H,br.s).

Anal. Calcd. (%) for C₁₈H₂₈O₄: C 70.10, H 9.15. Found (%): C 69.74, H 9.14.

PREPARATION OF INTERMEDIATE

3. Methyl (+)-5(Z)-7-[(1R, 2S, 3S, 5S)-2-(tert-butoxycarbonylamino)-6,6-dimethylbicyclo[3.1.1]hept-3-yl]-5-heptenoate 4a

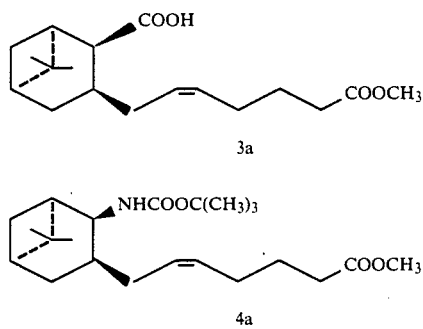

To a solution of 2.063 g of carboxylic acid 3a [prepared in 2-(1)] in 8 ml of acetone and 1.5 ml of water are dropwise added a solution of 1.4 ml of triethylamine in 3 ml of acetone, and a solution of 1.0 g of ethyl chlorocarbonate in 2 ml of acetone, successively, at 0° C. under stirring and the mixture is stirred at the same temperature for 1 hour. A solution of 1.0 g of sodium azide in 4 ml of water is added and the mixture is stirred at 0° C. for 1 hour. To the reaction mixture is added 10 ml of water and the mixture is extracted with ethyl ether. The extract is washed with water, dried over anhydrous sodium sulfate and evaporated under reduced pressure. The residue is dissolved in 50 ml of benzene, then refluxed for 30 minutes with heating, and evaporated. The residue is dissolved in 30 ml of tert-butyl alcohol, further refluxed with heating for 72 hours and evaporated. The resulting residue is purified by frash column chromatography (45 g of silica gel, 230–400 mesh, eluted with hexane-ethyl acetate=6:1) to give the titled compound 4a as an oil.

Each compound 3b, 3c and 3e is allowed to react in the same manner as mentioned above to give compound 4b, 4c and 4e, respectively. The results are shown in Table 1.

TABLE 1

| Compound | Yd. (%) | Specific rotation $[\alpha]_D$ | IR ν max (film) [cm$^{-1}$] | NMR δ ppm(CDCl$_3$) | Elementary analysis (for C$_{22}$H$_{27}$NO$_4$) |
|---|---|---|---|---|---|
| 4a (structure with NHCOOC(CH$_3$)$_3$ and COOCH$_3$) | 44.1 | +43.3° (22° C., c 1.191 CH$_3$OH) | 3460, 3390, 1741, 1713, 1512, 1504 | 0.94 (3H,s), 0.94 (1H,d,J=10Hz), 1.02 (3H,s), 1.43 (9H,s), 1.3~2.6 (14H), 3.68 (3H,s), 4.30 (1H,t, J=9Hz), 4.80 (1H,d,J=9Hz), 5.40 (2H,m). | Calcd. (%): C 69.62, H 9.83, N 3.69. Found (%): C 69.69, H 9.86, N 3.24. |
| 4b (structure with NHCOOC(CH$_3$)$_3$ and COOCH$_3$) | 38.6 | +33.0° (22° C., c 1.302, CH$_3$OH) | 3460, 3400, 1740, 1723, 1499 | 0.82 (1H,d,J=10Hz), 1.01 (3H,s), 1.20 (3H,s), 1.43 (9H,s), 1.3~2.6 (14H), 3.65 (3H,s), 3.73 (1H,m), 4.09 (1H,d,J=9Hz), 5.40 (2H,m). | Calcd. (%): C 69.62, H 9.83, N 3.69. Found (%): C 69.31, H 9.86, N 3.64 |
| 4c (structure with NHCOOC(CH$_3$)$_3$ and COOCH$_3$) | 70.7 | −43.2° (22° C., c 0.975, CH$_3$OH) | 3390, 1741, 1715, 1510 | 0.83 (3H,s), 1.20 (3H,s), 1.42 (9H,s), 1.2~2.55 (15H), 3.67 (3H,s), 3.73 (1H,s), 4.55 (1H,d, J=9Hz), 5.43 (2H,m). | Calcd. (%): C 69.62, H 9.83, N 3.69. Found (%): C 69.33, H 9.80, N 3.71 |
| 4e (structure with NHCOOC(CH$_3$)$_3$ and COOCH$_3$) | 45.7 | −31.7° (23° C., c 1.036, CH$_3$OH) | Identical with 4b | Identical with 4b | |

EXAMPLE 1

Methyl (+)-5(Z)-7-[(1R, 2S, 3S, 5S)-2-(benzenesulfonamideo-6,6-dimethylbicyclo[3.1.1-]hept-3-yl]-5-heptenoate 5a-a

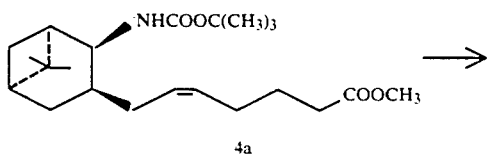

To 1.25 g of the BOC compound 4a (prepared in 3) is added 10 ml of trifluoroacetic acid at room temperature, the mixture is stirred for 30 minutes and the solvent is evaporated. The residue is dissolved in 15 ml of dichloromethane, 600 mg of benzenesulfonyl chloride and 3 ml of triethylamine are added thereto and the mixture is stirred at room temperature for 20 minutes. The reaction mixture is washed with water, dried over anhydrous sodium sulfate and evaporated. The residue is purified by frash column chromatography [45 g of silica gel, 230–400 mesh, eluted with hexane -ethyl acetate=4:1]. The eluate is evaporated to give crystals, which are washed with hexane to give the titled compound 5a-a.

Yield 78.6%.

Mp. 55° C.

$[\alpha]_D$+52.7° (23° C., c 1.094, CH$_3$OH).

IR ν max(KBr): 3280, 1735, 1337, 1320, 1167, 1157 cm$^{-1}$.

NMR δ ppm(CDCl$_3$): 0.84(3H,s), 0.96(1H,d,J=10 Hz), 1.07(3H,s), 1.2~2.5 (14H), 3.66(3H,s), 3.90(1H,m), 4.86(1H,d,J=10 Hz), 5.23(2H,m), 7.35~7.66 (3H,m), 7.80~7.91 (2H,m).

CD λ mm(Δε)CH$_3$OH: 269.5 (+0.297), 262.5 (+0.358), 255.5 (+0.345), 222 (+5.03).

Anal. Calcd. (%) for C$_{23}$H$_{33}$NO$_4$S: C 65.84, H 7.93, N 3.34, S 7.64. Found (%): C 65.77, H 7.85, N 3.34, S 7.59.

EXAMPLE 2

Methyl 5(Z)-7-[(1R,2R,3S,5S)-2-(3-chlorobenzenesulfonylamido)-6,6-dimethylbicyclo[3.1.1]hept-3-yl]-5-heptenoate 5b-f

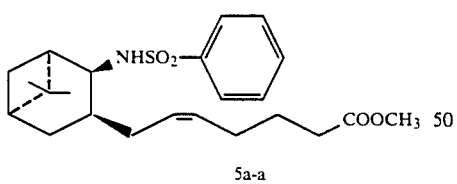

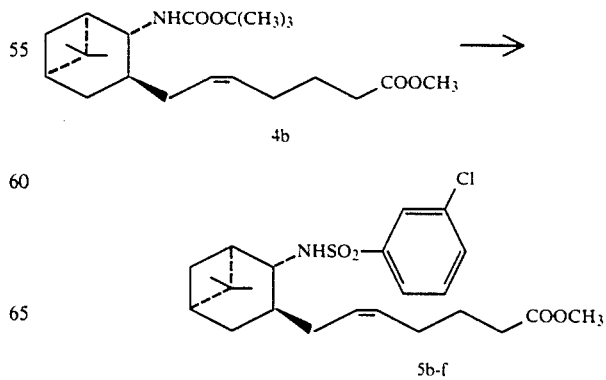

The compound 5b-f can be prepared in the same manner as in

EXAMPLE 1

To 0.5 ml of solution of 500 mg of BOC compound 4b (Table 1) in dichloromethane is added 1 ml of trifluoroacetic acid and the mixture is stirred for 30 minutes. The solvent is evaporated under reduced pressure and the residue is dissolved in ether. The resulting solution is washed with a 10% sodium carbonate aqueous solution, a saturated aqueous solution of sodium chloride, successively, dried on anhydrous sodium sulfate, and evaporated under reduced pressure. To the residue dissolved in 10 ml of dichloromethane is added 1 ml of triethylamine and 428 mg of 3-chlorobenzenesulfonyl chloride is added thereto at 0° C. The mixture is stirred for 1 hour. Ether is added to the reaction mixture, which is then washed with 10% hydrochloric acid, a saturated aqueous solution of sodium hydrogencarbonate and water, successively, dried on anhydrous sodium salfate, and distilled under reduced pressure. The residue is purified by frash column chromatography (25 g of silica gel, eluted with hexane-ethyl acetate=4:1) to give 576 mg of the titled compound 5b-f.

The results are shown in Table 2.

EXAMPLE 3-21

In the same manner as described in Example 1 or 2, the starting compound 4b, 4c or 4e of which amino protecting group is deprotected is allowed to react with benzenesulfonyl chloride, tosyl chloride, 4-fluorobenzenesulfonyl chloride, methanesulfonyl chloride, nitrobenzenesulfonyl chloride, 2-naphthylsulfonyl chloride, benzylsulfonyl chloride, 4-biphenylsulfonyl chloride, 4-metoxybenzenesulfonyl chloride, 3-phenylpropanesulfonyl chloride, 2-phenylethanesulfonyl chloride, 4-chlorobenzenesulfonyl chloride, 2-chlorobenzenesulfonyl chloride, 3-chlorobenzenesulfonyl chloride, 4-ethylbenzenesulfonyl chloride, or 4-acetoxybenzenesulfonyl chloride in the presence of triethylamine in dichloromethane.

The compounds shown in Table 2 are prepared.

TABLE 2

| Compound | Yd. (%) | Mp. [°C.] | Specific rotation [α]$_D$ | IR ν max [cm$^{-1}$] | NMR δ ppm(CDCl$_3$) | CD λ nm(Δε) (CH$_3$OH) | Analysis (for C$_{23}$H$_{33}$NO$_4$S) Calcd. (%) Found (%) |
|---|---|---|---|---|---|---|---|
| 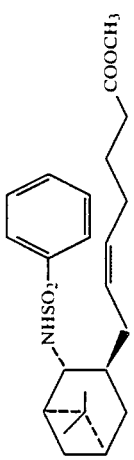 5b-a | 73.6 | | +29.5° (23° C., c 1.263, CH$_3$OH) | (Film) 3300, 1740, 1328, 1164 | 0.72 (1H,d,J=10Hz), 0.99 (3H,s), 1.08 (3H,s), 1.25~2.45 (14H), 3.37 (1H,m), 3.69 (3H,s), 4.94 (1H,d,J=8Hz), 5.31 (2H,m), 7.36~7.68 (3H,m), 7.86~7.97 (2H,m). | 279 (+0.033) 270 (+0.085) 264 (+0.115) 257 (+0.082) 247 (+0.091) 225 (+1.35) 200 (−2.89) | C 65.84, H 7.93, N 3.34, S 7.64, C 65.63, H 7.71, N 3.36, S 7.45. |
| 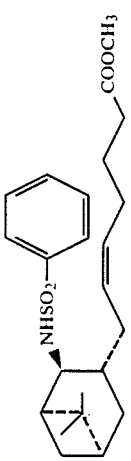 5c-a | 73.6 | | −24.6° (20° C., c 1.275, CH$_3$OH) | (Film) 3280, 1738, 1323, 1161 | 0.72 (3H,s), 1.07 (3H,s), 1.2~2.45 (15H), 3.34 (1H,t,J=8Hz), 3.69 (3H,s), 4.85 (1H,d,J=9Hz), 5.34 (2H,m), 7.37~7.65 (3H,m), 7.83~7.94 (2H,m). | 269 (+0.070) 262 (+0.106) 257sh (+0.118) 220 (+3.15) | C 65.84, H 7.93, N 3.34, S 7.64, C 65.93, H 7.93, N 3.36, S 7.56. |
| 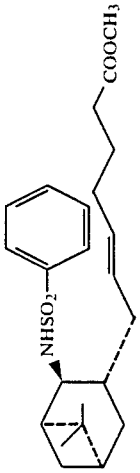 8c-a | 4.1 | 101~102 | −21.4° (20° C., c 0.800, CH$_3$OH) | (KBr) 3270, 1731, 1324, 1167 | 0.68 (3H,s), 1.06 (3H,s), 1.20~2.50 (15H), 3.32 (1H,t,J=8Hz), 3.66 (3H,s), 4.79 (1H,d,J=9Hz), 5.32 (2H,m), 7.37~7.70 (3H,m), 7.83~7.98 (2H,m). | 269 (+0.064) 262 (+0.091) 256sh (+0.109) 222 (+2.55) | C 65.84, H 7.93, N 3.34, S 7.64, C 65.64, H 7.88, N 3.29, S 7.52. |
| 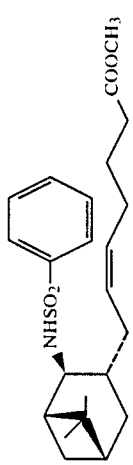 5e-a | 71.4 | | −29.0° (25° C., c 0.987, CH$_3$OH) | Identical with 5b. | Identical with 5b. | | C 65.84, H 7.93, N 3.34, S 7.64, C 65.74, H 8.01, N 3.36, S 7.52. |

TABLE 2-continued

| Compd. Number | | Yd. (%) | [α]$_D$ (CH$_3$OH) | IR ν max (film) cm$^{-1}$ | NMR δ ppm(CDCl$_3$) | Elementary Analysis (Molecular Formula) Calcd. (%) Found (%) |
|---|---|---|---|---|---|---|
| 5a-b | 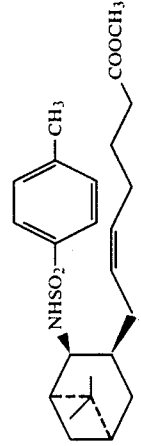 | 44.8 | +58.3° (23° C., c 0.978, CH$_3$OH) | (CHCl$_3$) 3395, 1732, 1341, 1155 | 0.84 (3H,s), 0.95 (1H,d,J=10Hz), 1.07 (3H,s), 1.2~2.6 (14H), 2.41 (3H,s), 3.67 (3H,s), 3.90 (1H,m), 4.88 (1H, d, J=9Hz), 5.35 (2H,m), 7.28 (2H, d, J=8Hz), 7.74 (2H,d,J=8Hz. | |
| 5b-c | 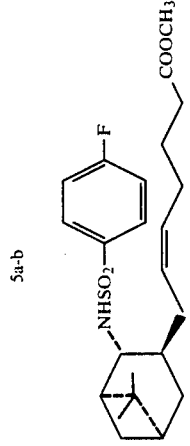 | 20.6 | +28.8° (23° C., c 1.760, CH$_3$OH) | (CHCl$_3$) 3395, 1730, 1340, 1165, 1154 | 0.72 (1H,d,J=10Hz), 1.00 (3H,s), 1.10 (3H,s), 1.1~2.6 (14H), 3.35 (1H,m), 3.69 (3H,s), 4.91 (1H,d,J=8Hz), 5.33 (2H,m), 7.23 (2H,d, J=9Hz), 7.90 (2H,dd,J=9, 5Hz). | |

4b 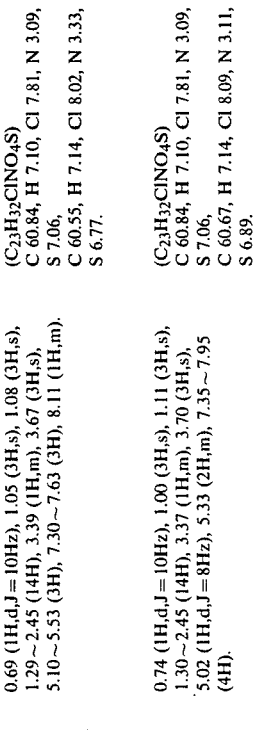 5b

| Compd. Number | R$_2$ | Yd. (%) | [α]$_D$ (CH$_3$OH) | IR ν max (film) cm$^{-1}$ | NMR δ ppm(CDCl$_3$) | Elementary Analysis (Molecular Formula) Calcd. (%) Found (%) |
|---|---|---|---|---|---|---|
| 5b-d | 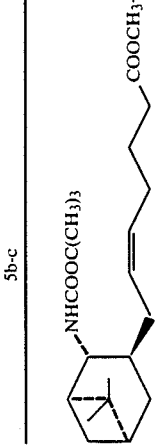 | 93.4 | +31.2° (26° C., c 1.308) | 3300, 1739, 1332, 1163. | 0.72 (1H,d,J=10Hz), 0.98 (3H,s), 1.09 (3H,s), 1.28~2.43 (14H), 3.33 (1H,m), 3.67 (3H,s), 5.12 (1H,d,J=8Hz), 5.30 (2H,m), 7.48 (2H,d, J=8Hz), 7.84 (2H,d,J=8Hz). | |
| 5b-e | 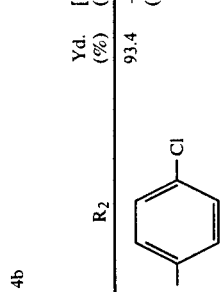 | 96.8 | −9.3° (25° C., c 1.684) | 3310, 1738, 1341, 1167. | 0.69 (1H,d,J=10Hz), 1.05 (3H,s), 1.08 (3H,s), 1.29~2.45 (14H), 3.39 (1H,m), 3.67 (3H,s), 5.10~5.53 (3H), 7.30~7.63 (3H), 8.11 (1H,m). | (C$_{23}$H$_{32}$ClNO$_4$S) C 60.84, H 7.10, Cl 7.81, N 3.09, S 7.06, C 60.55, H 7.14, Cl 8.02, N 3.33, S 6.77. |
| 5b-f | | 93.9 | +30.5° (25° C., c 1.233) | 3295, 1739, 1334, 1162. | 0.74 (1H,d,J=10Hz), 1.00 (3H,s), 1.11 (3H,s), 1.30~2.45 (14H), 3.37 (1H,m), 3.70 (3H,s), 5.02 (1H,d,J=8Hz), 5.33 (2H,m), 7.35~7.95 (4H). | (C$_{23}$H$_{32}$ClNO$_4$S) C 60.84, H 7.10, Cl 7.81, N 3.09, S 7.06, C 60.67, H 7.14, Cl 8.09, N 3.11, S 6.89. |

TABLE 2-continued

| | | | | | |
|---|---|---|---|---|---|
| 5b-g | ![p-ethylphenyl] | 89.1 | +28.8° (25° C., c 1.945) | 3300, 1740, 1327, 1161. | 0.72 (1H,d,J=10Hz), 1.01 (3H,s), 1.10 (3H,s), 1.25 (3H,t,J=7.6Hz), 1.40~2.42 (14H), 2.71 (2H,q,J=7.6Hz), 3.35 (1H,m), 3.69 (3H,s), 4.82 (1H,d,J=8Hz), 5.29 (2H,m), 7.31 (2H,d, J=8Hz), 7.77 (2H,d,J=8Hz). | (C₂₅H₃₇NO₄S) C 67.08, H 8.33, N 3.13, S 7.16, C 66.92, H 8.44, N 3.16, S 6.86. |
| 5b-h | ![p-nitrophenyl] | 97.6 | +33.4° (25° C., c 1.070) | (film) 3295, 1739, 1531, 1350, 1165. | 0.75 (1H,d,J=10Hz), 1.02 (3H,s), 1.11 (3H,s), 1.30~2.50 (14H), 3.40 (1H,m), 3.69 (3H,s), 5.10~5.50 (3H,s), 8.05 (2H,d,J=9Hz), 8.35 (2H,d,J=9Hz). | (C₂₃H₃₂N₂O₆S) C 59.46, H 6.94, N 6.03, N 6.90, C 59.15, H 7.00, N 6.07, S 6.62. |
| 5b-i | ![p-methoxyphenyl] | 96.7 | +27.9° (25° C., c 1.218) | (film) 3285, 1738, 1324, 1156. | 0.71 (1H,d,J=10Hz), 1.00 (3H,s), 1.10 (3H,s), 1.27~2.50 (14H), 3.33 (1H,m), 3.68 (3H,s), 3.87 (3H,s), 4.91 (1H,d,J=8Hz), 5.32 (2H,m), 6.96 (2H,d,J=9Hz), 7.82 (2H,d,J=9Hz). | (C₂₄H₃₅NO₅S) C 64.11, H 7.85, N 3.12, S 7.13, C 63.61, H 7.86, N 3.17, S 7.05. |
| 5b-j | ![p-acetoxyphenyl] Ac: Acetyl | 12.2 | | (film) 3294, 1774, 1738, 1330, 1195, 1157. | 0.72 (1H,d,J=10Hz), 1.01 (3H,s), 1.11 (3H,s), 1.26~2.50 (14H), 2.33 (3H,s), 3.33 (1H,m), 3.67 (3H,s), 5.16 (1H,d,J=8Hz), 5.30 (2H,m), 7.22 (2H,d,J=9Hz), 7.88 (2H,d,J=9Hz). | (C₂₅H₃₅NO₆S) C 62.87, H 7.39, N 2.93, S 6.71, C 62.74, H 7.46, N 3.26, S 6.35. |
| 5b-b | ![p-tolyl] | 80.8 | +30.7° (25° C., c 1.157) | 3290, 1740, 1325, 1162. | 0.72 (1H,d,J=10Hz), 1.01 (3H,s), 1.10 (3H,s), 1.26~2.5 (12H), 2.28 (2H,t,J=7Hz), 2.41 (3H, s), 3.32 (1H,m), 3.68 (3H,s), 4.78 (1H,d, J=8Hz), 5.30 (2H,m), 7.29 (2H,d,J=8Hz), 7.75 (2H,d,J=8Hz). | |
| 5b-l | ![biphenyl] | 95.3 | +32.9° (25° C., c 1.024) | (KBr) 3280, 1731, 1325, 1160. | 0.75 (1H,d,J=10.2Hz), 1.03 (3H,s), 1.11 (3H, s), 1.42 (1H,m), 1.55~2.31 (11H), 2.27 (2H,t, J=7.4Hz), 3.40 (1H,m), 3.67 (3H,s), 4.85 (1H, d,J=8.4Hz), 5.32 (2H,m), 7.38~7.64 (5H), 7.72 (2H,d,J=8.7Hz), 7.93 (2H,d,J=8.7Hz). | (C₂₇H₃₇NO₄S) C 70.27, H 7.52, N 2.83, S 6.47, C 70.38, H 7.58, N 2.93, S 6.40. (Mp.; 86~87° C.) |
| 5b-m | ![naphthyl] | 96.3 | +12.4° (25° C., c 1.810) | 3295, 1738, 1327, 1160. | 0.71 (1H,d,J=10Hz), 1.03 (3H,s), 1.07 (3H,s), 1.30~2.40 (14H), 3.40 (1H,m), 3.67 (3H,s), 5.05 (1H,d,J=8Hz), 5.22 (2H,m), 7.50~8.10 (6H), 8.45 (1H,s). | (C₂₅H₃₅NO₄S) C 69.05, H 7.51, N 2.98, S 6.83, C 68.68, H 7.56, N 3.03, S 6.60. |
| 5b-n | —CH₃ | 76.7 | +37.7° (25° C., c 1.285) | 3300, 1738, 1322, 1152. | 0.85 (1H,d,J=10.2Hz), 1.06 (3H,s), 1.24 (3H, s), 1.49 (1H,ddd,J=2.7,5.3,13.2Hz), 1.70 (2H,quint,J=7.3Hz), 1.83~2.39 (8H), 2.34 (2H,t,J=7.3Hz), 2.48 (1H,td,J=4.5,13.8Hz), 2.79 (3H,s), 3.51 (1H,ddd,J=2.7,6.0,8.5Hz), 3.68 (3H,s), 4.55 (1H,d,J=8.6Hz), 5.46 (2H, m). | |

TABLE 2-continued

| | | | | | |
|---|---|---|---|---|---|
| 5b-o | —CH₂—⌬ | 57.8 | +18.0° (25° C., c 1.991) | 3305, 1738, 1320, 1153. | 0.81 (1H,d,J=10Hz), 0.93 (3H,s), 1.22 (3H, s), 1.30~2.60 (14H), 3.52 (1H,m), 3.63 (3H, s), 4.21 (2H,s), 4.38 (1H,d,J=9Hz), 5.42 (2H, m), 7.39 (5H,s). | (C₂₄H₃₅NO₄S) C 66.48, H 8.14, N 3.23, S 7.40, C 66.22, H 8.19, N 3.36, S 7.26. |
| 5b-p | —(CH₂)₂—⌬ | 78.9 | +33.0° (26° C., c 1.313) | 3300, 1738, 1320, 1149. | 0.82 (1H,d,J=10Hz), 1.03 (3H,s), 1.21 (3H, s), 1.33~2.70 (14H), 2.96~3.40 (4H), 3.50 (1H,m), 3.65 (3H,s), 4.54 (1H,d,J=9Hz), 5.44 (2H,m), 7.10~7.46 (5H). | (C₂₅H₃₇NO₄S) C 67.08, H 8.33, N 3.13, S 7.16, C 66.92, H 8.36, N 3.28, S 7.01. |
| 5b-q | —(CH₂)₃—⌬ | 60.1 | +27.7° (26° C., c 1.890) | 3295, 1739, 1322, 1148. | 0.78 (1H,d,J=10Hz), 1.01 (3H,s), 1.19 (3H, s), 1.30~3.10 (20H), 3.44 (1H,m), 3.65 (3H,s), 4.48 (1H,d,J=9Hz), 5.41 (2H,m), 7.06 ~7.45 (5H). | (C₂₆H₃₉NO₄S) C 67.64, H 8.52, N 3.03, S 6.95, C 67.34, H 8.46, N 3.19, S 6.89. |

EXAMPLE 22

(+)-5(Z)-7-[(1R, 2S, 3S, 5S)-benzenesulfonamido-6,6-dimethylbicyclo[3.1.1-]hept-3-yl]-5-heptenoic acid 6a—a and its sodium salt 7a—a

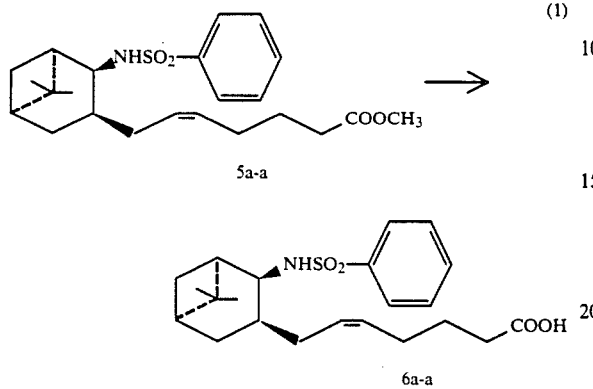

To a solution of 1.58 g of methyl ester 5a—a (prepared in Example 1) in 20 ml of methanol is added 8 ml of 10% aqueous solution of sodium hydroxide and the mixture is stirred at room temperature for 2 hours. The reaction mixture is acidified with 10% hydrochloric acid, extracted with ether, washed with water, dried over anhydrous sodium sulfate and evaporated. The residue is purified by frash column chromatography [20 g of silica gel, 230–400 mesh, eluted with hexane—ethyl acetate=2:1 to 1:1] to give titled compound 6a—a as an oil.

Yield 95.3%.

$[\alpha]_D$+48.7° (23° C., c 1.513, CH₃OH).

IR ν max(CHCl₃): 3520, 3395, 3265, 1710, 1342, 1158 cm$^{-1}$.

NMR δ ppm(CDCl₃): 0.85(3H,s), 0.98(1H,d,J=10 Hz), 1.07(3H,s), 1.3~2.5 (14H), 3.91(1H,m), 5.23(1H,d,J=7 Hz), 5.33(2H,m), 7.33~7.63 (3H,m), 7.80~7.91(2H,m), 8.15 (1H,br.s).

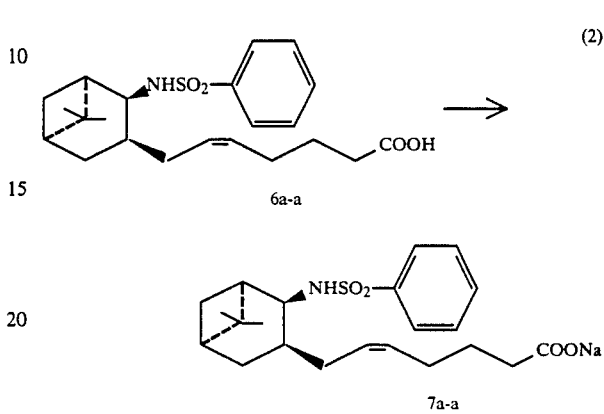

To a solution of 1.676 g of the above carboxylic acid 6a—a in 10 ml of methanol is added 18.2 ml of 0.221M solution of sodium methylate in methanol and the solvent is evaporated under reduced pressure. The residue is dissolved in 30 ml of water, treated with active carbon and then lyophilized to give the titled compound 7a—a as powder.

IR ν max(KBr): 3300, 1560, 1338, 1308, 1153 cm$^{-1}$.

EXAMPLE 23-43

(1) The reaction is carried out in the same as in Example 22-(1) to yield the compounds shown in Table 3.

TABLE 3

| Compound | Yield (%) | Specific rotation $[\alpha]_D^{23}$ | IR $\nu_{max}$ [cm$^{-1}$] | NMR δ ppm(CDCl$_3$) |
|---|---|---|---|---|
| 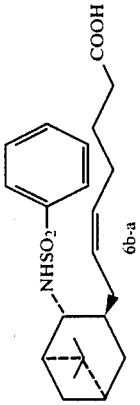 6b-a | 92.8 | +32.9° (c 1.278, CH$_3$OH) | (CHCl$_3$) 3520, 3395, 3275, 1710, 1331, 1160 | 0.71(1H, d, J=10Hz), 0.99(3H, s), 1.07(3H, s), 1.3~2.45 (14H), 3.35 (1H, m), 5.23(1H, d, J=7Hz), 5.32(2H, m), 7.35~7.63(3H, m), 7.75 (1H, br.s), 7.83~7.94(2H, m). |
| 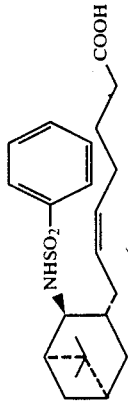 6c-a | quant. | −29.6° (c 0.945, CH$_3$OH) | (Film) 3280, 1709, 1324, 1163 | 0.71(3H, s), 1.07(3H, s), 1.2~2.5(15H), 3.31 (1H, m), 5.17(1H, d, J=9Hz), 5.35(2H, m), 7.4~ 7.6(3H, m), 7.7~8.0(2H, m), 8.37(1H, br.s). |
| 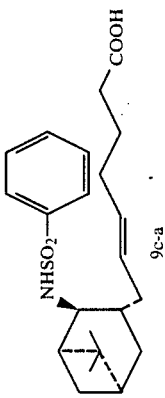 9c-a | quant. | | | 0.69(3H, s), 1.06(3H, s), 1.20~2.50(15H), 3.32(1H, t, J=8Hz), 5.08(1H, d, J=9Hz), 5.33 (2H, m), 7.37~7.69(3H, m), 7.83~7.94(2H, m), 8.53(1H, br.s). |
| 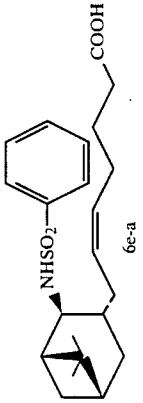 6e-a | 77.9 | −30.5° (c 0.798, CH$_3$OH) | Identical with Compound 6b. | Identical with Compound 6b. |
| 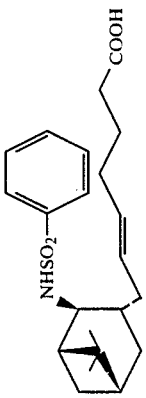 9e-a | 1.8 | −29.4° (c 0.640, CH$_3$OH) | | |
| 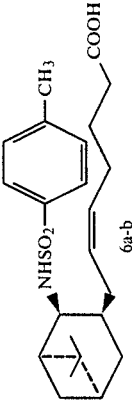 6a-b | quant. | | | 0.84(3H, s), 0.97(1H, d, J=10Hz), 1.07(3H, s), 1.2~2.65(14H), 2.40(3H, s), 3.90(1H, m), 5.18(1H, d, J=9Hz), 5.34(2H, m), 7.26(2H, d, J=8Hz), 7.71(2H, d, J=8Hz), 8.40(1H, br.s) |

TABLE 3-continued

| Compd. Number | R₂ | Yd. (%) | [α]_D (CH₃OH) | IR ν_max (film) cm⁻¹ | NMR δ ppm (CDCl₃) | CD λnm (Δε) (CH₃OH) Mp. (°C.) | Analysis (for M.W.) Calcd. (%) Found (%) |
|---|---|---|---|---|---|---|---|
| 6b-c | (structure with F, NHSO₂, COOH) | quant. | | | 0.70(1H, d, J=10Hz), 0.99(3H, s), 1.08(3H, s), 1.2~2.5(14H, m), 3.35(1H, m), 5.24(1H, d, J=9Hz), 5.34(2H, m), 7.21(2H, d, J=9Hz), 7.50(1H, br.s), 787(2H, dd, J=9, 6Hz). | | |
| 6b-d | 4-Cl-phenyl | 95.2 | +32.0° (25° C., c 1.158) | 3285, 1709, 1330, 1162. | 0.71(1H, d, J=10.3Hz), 0.99(3H, s), 1.07(3H, s), 1.45(1H, ddd, J=2.2, 5.0, 13.2Hz), 1.57~2.42(11H), 2.38(2H, t, J=6.9Hz), 3.38(1H, ddd, J=2.2, 5.5, 8.0Hz), 5.29~5.48(3H), 7.48(2H, d, J=8.8Hz), 7.82(2H, d, J=8.8 Hz). | (CH₃OH) 276 (+0.139), 268.5 (+0.170), 235 (+1.548). | |
| 6b-e | 2-Cl-phenyl | 99.1 | −5.6° (25° C., c 1.965) | 3295, 1708, 1333, 1162. | 0.69(1H, d, J=10.2Hz), 1.07(6H, s), 1.43(1H, ddd, J=2.5, 4.7, 13.0Hz), 1.58~2.42(11H), 2.37(2H, t, J=7.1Hz), 3.41(1H, ddd, J=2.8, 5.0, 9.0Hz), 5.36(2H, m), 5.53(1H, d, J=9.0Hz), 7.36~7.55(3H), 8.09(1H, m). | (CH₃OH) 277.5 (−0.188), 270 (−0.215), 261.5 (−0.194), 226 (−2.03). | |
| 6b-f | 3-Cl-phenyl | 98.5 | +34.2° (25° C., c 1.238) | 3285, 1709, 1332, 1162. | 0.72(1H, d, J=10.3Hz), 1.00(3H, s), 1.08(3H, s), 1.45(1H, ddd, J=2.2, 5.2, 13.2Hz), 1.57~2.32(11H), 2.38(2H, t, J=6.9Hz), 3.40(1H, dd, J=2.0, 6.0, 8.0Hz), 5.29~5.50(3H), 7.45(1H, t, J=7.7Hz), 7.54(1H, td, J=1.7, 8.2Hz), 7.76(1H, dd, J=1.4, 7.5Hz), 7.87(1H, t, J=1.9Hz). | (CH₃OH) 276 (−0.0242), 269 (−0.0273), 232 (+2.336). | |
| 6b-g | 4-C₂H₅-phenyl | 87.9 | +30.8° (25° C., c 0.941) | 3280, 1710, 1322, 1160. | 0.70(1H, d, J=10.2Hz), 0.99(3H, s), 1.04(3H, s), 1.25(3H, t, J=7.6Hz), 1.43(1H, ddd, J=2.0, 5.0, 13.5Hz), 1.56~2.42(11H), 2.37(2H, t, J=6.9Hz), 2.72(2H, q, J=7.6Hz), 3.38(1H, ddd, J=2.2, 5.8, 8.0Hz), 5.27(1H, d, J=8.0Hz)5.28~5.46(2H), 7.32(2H, d, J=8.5Hz), 7.78(2H, d, J=8.5Hz). | (CH₃OH) 271.5 (+0.118), 265 (+0.136), 258 (+0.115), 230 (+1.336). | |

TABLE 3-continued

| | | | | | | |
|---|---|---|---|---|---|---|
| 6b-h | ![4-nitrophenyl] | 95.6 | +33.2° (25° C., c 1.060) | (KBr) 3285, 1705, 1533, 1350, 1309, 1165. | 0.73(1H, d, J=10.3Hz), 0.99(3H, s), 1.06(3H, s), 1.46(1H, ddd, J=2.5, 5.3, 13.1Hz), 1.56~2.32(11H), 2.39(2H, t, J=6.8Hz), 3.44(1H, ddd, J=2.5, 5.5, 8.0Hz), 5.40(2H, m), 5.65(1H, d, J=8.0Hz), 8.07(2H, d, J=9.1Hz), 8.37(2H, d, J=9.1Hz). | (CH₃OH) 291 (+0.409), 242 (-0.133), 222 (+0.267), 75-78 | (C₂₂H₃₀N₂O₆S) C 58.65, H 6.71, N 6.22, S 7.12, C 58.66, H 6.83, N 6.12, S 7.09. |
| 6b-i | ![4-methoxyphenyl] | 93.1 | +30.3° (25° C., c 1.503) | (film) 3285, 1708, 1322, 1154. | 0.70(1H, d, J=10.4Hz), 1.00(3H, s), 1.08(3H, s), 1.44(1H, m), 1.55~2.30(11H), 2.37(2H, t, J=6.9Hz), 3.32(1H, m), 3.87(3H, s), 5.28(1H, d, J=7.9Hz), 5.29~5.48(2H), 6.97(2H, d, J=9.0Hz), 7.80(2H, d, J=9.0Hz). | (CH₃OH) 277 (+0.2221), 270.5 (+0.245), 240 (+0.455), 208 (+2.72). | |
| 6b-k | ![4-hydroxyphenyl] | 64.6 | -34.3° (25° C., c 0.865) | (KBr) 17.08, 1318, 1152, 1144. | 0.71(1H, d, J=10.2Hz), 1.01(3H, s), 1.12(3H, s), 1.42(1H, ddd, J=2.2, 5.2, 13.2Hz), 1.58~2.29(11H), 2.36(2H, t, J=6.9Hz), 3.25(1H, ddd, J=2.4, 5.8, 8.0Hz), 5.14(1H, d, J=8.0Hz), 6.92(2H, d, J=8.9 Hz), 7.74(2H, d, J=8.9Hz). | (CH₃OH) 278sh (+0.324), 274 (+0.376), 241 (+0.439), 208.5 (+1.99). 95-96 | (C₂₂H₃₁NO₆S) C 62.68, H 7.41, N 3.32, S 7.61, C 62.59, H 7.45, N 3.41, S 7.39. |
| 6b-b | ![4-methylphenyl] | 43.6 | +33.7° (26° C., c 0.891) | (CHCl₃) 3400, 3270, 1335, 1159. | 0.70(1H, d, J=10.2Hz), 1.00(3H, s), 1.06(3H, s), 1.42(1H, m), 1.55~245(11H), 2.37(2H, t, J=7.0Hz), 2.42(3H, s), 3.36(1H, m), 5.29 (1H, d, J=7.6Hz), 5.37(2H, m), 7.29(2H, d, J=8.3Hz), 7.75(2H, d, J=8.3Hz). | (CH₃OH) 273 (+0.106), 266 (+0.118), 261 (+0.103), 230 (+1.69). 79-80 | (C₂₃H₃₃NO₄S) C 65.84, H 7.93, N 3.34, S 7.64, C 65.61, H 7.95, N 3.60, S 7.39. |
| 6b-l | ![biphenyl] | 95.3 | +33.0° (25° C., c 1.048) | (KBr) 3275, 1712, 1323, 1161. | 0.72(1H, d, J=10.2Hz), 1.01(3H, s), 1.06(3H, s), 1.45(1H, m), 1.52~2.40(11H), 2.36(2H, t, J=6.9Hz), 3.42(1H, ddd, J=2.0, 5.6, 8.0Hz), 5.27~5.50(3H), 7.37~7.53(3H), 7.58~7.67 (2H), 7.72(2H, d, J=8.6Hz), 7.94(2H, d, J=8.6Hz). | (CH₃OH) 262 (-0.252), 255 (-0.300), 216 (+5.00). 111~113 | (C₂₈H₃₅NO₄S) C 69.82, H 7.32, N 2.91, S 6.66, C 69.50, H 7.28, N 2.83, S 6.39. |
| 6b-m | ![naphthyl] | 99.0 | +13.0° (25° C., c 1.117) | (CH₃Cl) 3390, 3260, 1710, 1332, 1156. | 0.69(1H, d, J=10.2Hz), 1.02(6H, s), 1.42(1H, ddd, J=2.0, 5.2, 13.0Hz), 1.52~2.35(11H), 2.31(2H, t, J=6.9Hz), 3.41(1H, ddd, J=2.1, 6.0, 8.0Hz), 5.21~5.40(2H), 5.45(1H, d, J=8.0Hz), 7.62(2H, m), 7.82~7.99(4H), 8.44(1H, d, J=1.4 Hz). | (CH₃OH) 321.5 (+0.203), 307.5 (+0.161), 292.5 (+0.382), 268 (-0.773), 228 (-4.73), 224 (-5.30). | |
| 6b-n | —CH₃ | 92.2 | +36.5° (25° C., c 0.896) | (film) 32.85, 1709, 1320, 1151. | 0.83(1H, d, J=10.1Hz), 1.07(3H, s), 1.24(3H, s), 1.52(1H, dd, J=2, 5, 5, 13.2Hz), 1.58~2.39(10Hz), 2.38(2H, t, J=6.9Hz), 2.56(1H, m), 2.98(3H, s), 3.52(1H, ddd,J=2.5, 6.0 8.0Hz), 5.10(1H, d, J=8.0Hz), 5.48(2H, m). | C 59.45, H 8.51, | (C₁₇H₂₉NO₄S) N 4.08, S 9.34, C 58.93, H 8.42, N 4.06, S 8.92. |

TABLE 3-continued

| | | | | | |
|---|---|---|---|---|---|
| 6b-o | 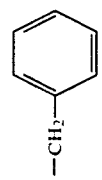—CH$_2$— | 96.1 | +18.3°<br>(25° C., c 1.162) | (film)<br>3290,<br>1708,<br>1318,<br>1152. | 0.80(1H, d, J=10.4Hz), 0.93(3H, s), 1.21(3H, s), 1.48(1H, ddd, J=2.5, 5.5, 13.3Hz), 1.56~2.40(10H), 2.35(2H, t, 6.9Hz), 2.55(1H, ddd, J=3.4, 6.8, 12.8Hz), 3.57(1H, m), 4.21 (1H, d, J=13.8Hz), 4.29(1H, d, J 32 13.9Hz), 4.86 (1H, d, J=8.3Hz), 5.46(2H, m), 7.39(5H, m). | (CH$_3$OH)<br>262 (−0.00303),<br>257 (−0.00424),<br>251.5 (−0.00424),<br>245 (−0.00364),<br>210 (−0.424). |
| 6b-p | 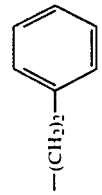—(CH$_2$)$_2$— | 89.3 | +30.5°<br>(25° C., c 1.133) | (film)<br>3290,<br>1709,<br>1318,<br>1150. | 0.82(1H, d, J=10.2Hz), 1.07(3H, s), 1.23(3H, s), 1.51(1H, ddd, J=2.6, 5.3, 13.1Hz), 1.61~2.42(10H), 2.37(2H, t, J=7.0Hz), 2.60(1H, m), 3.07~3.36(4H), 3.54(1H, ddd, J=2.5, 6.0, 8.2 Hz), 5.09(1H, d, J=8.2Hz), 5.35~5.60(2H) 7.28~7.38(5H). | (CH$_3$OH)<br>280 (+0.00364),<br>209 (+0.555). |
| 6b-q | 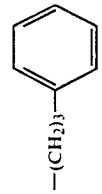—(CH$_2$)$_3$— | 46.3 | +30.6°<br>(25° C., c 0.900) | (film)<br>3290,<br>1710,<br>1320,<br>1148. | 0.78(1H, d, J=10.2Hz), 1.05(3H, s), 1.20(3H, s), 1.50(1H, ddd, J=2.0, 5.5, 13.0Hz), 1.58~2.42(12H), 2.36(2H, t, J=6.7Hz), 2.59(1H, t, J=8.5Hz), 2.65(2H, t, J=7.4Hz), 2.99(2H, m), 3.47(1H, m), 5.25(1H, d, J=8.2Hz), 5.33~5.61 (2H), 7.15~7.35(5H). | (CH$_3$OH)<br>260 (−0.00515),<br>253 (−0.00455),<br>245 (−0.00303). |

(2) The reaction is carried out in the same manner as in Example 22-(2) to yield the compounds shown in Table 4.

TABLE 4

| Compound | IR νmax(KBr)[cm$^{-1}$] |
|---|---|
| Sodium salt of 6b-a; 7b-a | 3295, 1563, 1325, 1310, 1162 |
| Sodium salt of 6c-a; 7c-a | 3280, 1565, 1323, 1308, 1162 |
| Sodium salt of 9c-a; 10c-a | 3280, 1560, 1322, 1308, 1161, 968 |
| Sodium salt of 6e-a; 7e-a | Identical with 7c |
| Sodium salt of 9e-a; 10e-a | 3290, 1562, 1321, 1308, 1160, 967 |
| Sodium salt of 6a-b; 7a-b | 3295, 1565, 1339, 1318, 1303, 1157. |
| Sodium salt of 6b-c; 7b-c | 3300, 1591, 1566, 1330, 1165, 1153. |

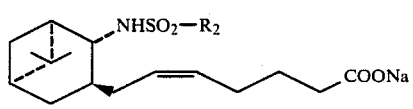
7b

| Compd. Number | R$_2$ | IR νmax(KBr) [cm$^{-1}$] |
|---|---|---|
| 7b-d | 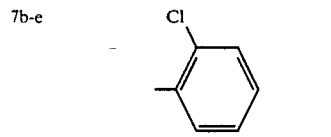 | 3290, 1563, 1325, 1160. |
| 7b-e | 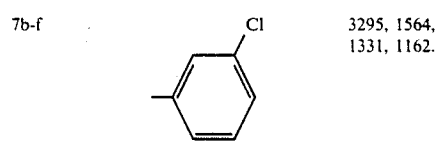 | 3320, 1561, 1333, 1162. |
| 7b-f | 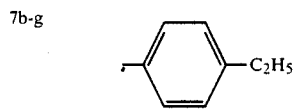 | 3295, 1564, 1331, 1162. |
| 7b-g | 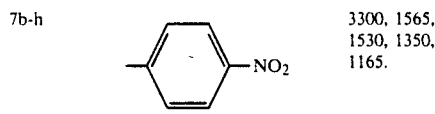 | 3290, 1565, 1320, 1159. |
| 7b-h | 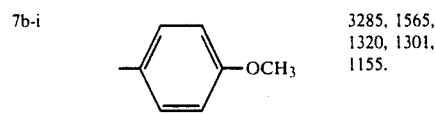 | 3300, 1565, 1530, 1350, 1165. |
| 7b-i | 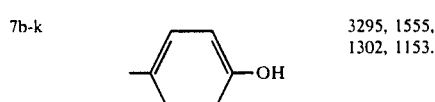 | 3285, 1565, 1320, 1301, 1155. |
| 7b-k | 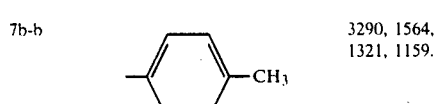 | 3295, 1555, 1302, 1153. |
| 7b-b | -⟨C$_6$H$_4$⟩-CH$_3$ | 3290, 1564, 1321, 1159. |

TABLE 4-continued

| 7b-l | (biphenyl) | 3295, 1562, 1320, 1157. |
|---|---|---|
| 7b-m | (naphthyl) | 3290, 1560, 1328, 1158. |
| 7b-n | —CH$_3$ | 3300, 1564, 1318, 1150. |
| 7b-o | —CH$_2$—⟨C$_6$H$_5$⟩ | 3295, 1564, 1317, 1151. |
| 7b-p | —(CH$_2$)$_2$—⟨C$_6$H$_5$⟩ | 3300, 1567, 1319, 1307, 1149. |
| 7b-q | —(CH$_2$)$_3$—⟨C$_6$H$_5$⟩ | 3295, 1565, 1319, 1303, 1148. |

PREPARATION OF INTERMEDIATE 4. (1R, 3RS, 5R)-3-(2-propenyl)-6,6-dimethylbicyclo[3.1.1]heptan-2-one 12

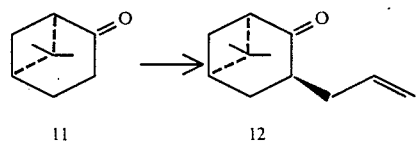

11    12

In nitrogen atmosphere, 115 ml of 1.6M solution of n-butyllithium in hexane is dropwise added to a solution of 30 ml of diisopropylamine in 40 ml of dry tetrahydrofuran at −30° C. After the mixture is stirred at −20° C. for 5 minutes, a solution of 18.9 g of (+)-nopinone 11 in 20 ml of dry tetrahydrofuran is dropwise added at −30° C. After stirred at 0° C. for 10 minutes, the mixture is cooled to −30° C. Then a solution of 17.5 ml of allyl bromide in 10 ml of dry tetrahydrofuran is dropwise added. After stirred at 35° C. for 30 minutes, the reaction mixture is poured into dilute hydrochloric acid undere ice cooling. After the organic layer is separated, the aqueous layer is extracted with ether. The combined organic layers are washed with an aqueous solution of sodium hydrogencarbonate and water, successively, dried over anhydrous sodium sulfate, and evaporated under reduced pressure. The residue is fractionally distilled through a fractionation column of about 10 cm length to give 1.90 g of the starting material at 61°-65° C./8 mmHg and 16.1 g of the titled compound 12 at 60°-78° C./5 mmHg in 13.8% and 66.0% yield, respectively. It is considered that the titled compound 12 is a mixture of epimers at 3-position.

Anal. Calcd. (%) for C$_{12}$H$_{18}$O: C, 80.85; H, 9.96. Found (%): C, 80.59; H, 9.96.

The residue is purified by frash chromatography [60 g of silica gel, 230-400 mesh, eluted with hexane—ether=10:1] to give 1.10 g of the dipropenyl compound in 3.7% yield.

$[\alpha]_D+56.4°$ (23° C., c 1.172, CHCl$_3$).

IR $\nu$ max(film): 1704 cm$^{-1}$.

NMR $\delta$ ppm(CDCl$_3$): 0.85(3H,s), 1.35(3H,s), 1.8~2.9(10H), 4.8~5.3(4H,m), 5.5~6.2(2H,m).

Anal. Calcd. (%) for C$_{15}$H$_{22}$O: C, 82.52; H10.16. Found (%): C, 81.69; H, 9.91.

PREPARATION OF INTERMEDIATE

5. O-Methyl oximes of (+)-(1R, 3S, 5S)- and (+)-(1R, 3R, 5S)-3-(2-propenyl)-6,6-dimethylbicyclo[3.1.1]heptan-2-ones 13a and 13b

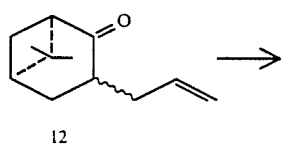

12

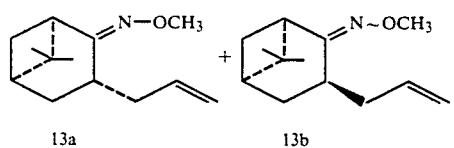

13a     13b

A mixture of 22.6 g of ketone 12 (prepared in 4), 23.8 g of O-methylhydroxylamine hydrochloride, 25 ml of pyridine and 300 ml of ethanol is refluxed with heating for 18 hours and then concentrated under reduced pressure to about ⅓ volume. Ice water is added and the mixture is acidified with dilute hydrochloric acid and extracted with ethyl acetate. The extract is washed with an aqueous solution of sodium hydrogencarbonate and water, successively, dried over anhydrous sodium sulfate, and evaporated under reduced pressure. The residue is separated into three isomers shown in Table 5 by frash chromatography (450 g of silica gel, 230-400 mesh, eluted with hexane—ether=20:1 to 10:1). In the second and third eluates, either syn or anti isomer of compound 13b is eluated.

TABLE 5

|  | 1st Eluate 13a | 2nd Eluate 13b | 3rd Eluate 13b |
|---|---|---|---|
| Yield | 43.4% | 11.8% | 16.0% |
| $[\alpha]_D^{24}$ (CHCl$_3$) | +23.4 (c 1.054) | +122.0 (c 1.388) | +65.2 (c 2.127) |
| IR $\nu$max (Film) | 1641, 1064 cm$^{-1}$ | 1641, 1060 cm$^{-1}$ | 1640, 1055 cm$^{-1}$ |
| NMR (CDCl$_3$) $\delta$ | 0.71 (3H, s), 1.29 (3H, s), 1.4~1.7 (2H, m), 1.8~2.4 (4H, m), 2.5~3.0 (2H, m), 3.41 (1H, t, J=6Hz), 4.9~5.3 (2H, m), 5.7~6.2 (1H, m). | 0.80 (3H, s), 1.30 (3H, s), 1.31 (1H, d, J=10Hz), 1.5~2.9 (7H), 3.45 (1H, t,J=6 Hz), 3.79 (3H, s), 4.9~5.2 (2H, m), 5.6~6.1 (1H, m). | 0.78 (3H, s), 1.28 (3H, s), 1.46 (1H, d, J=10Hz), 1.5~3.1 (8H, m), 3.72 (3H, s), 4.9~5.2 (2H, m), 5.6~6.1 (1H, m). |
| Anal. for C$_{13}$H$_{21}$NO | Calcd. (%): C, 75.32; H. 10.21; N, 6.76. Found (%): C, 74.91; H. 10.41; | Calcd. (%): C, 75.32; H. 10.21; N, 6.76. Found (%): C, 75.32; H. 10.39; | Calcd. (%): C, 75.32; H. 10.21; N, 6.76. Found (%): C, 74.97; H. 10.21; |

TABLE 5-continued

|  | 1st Eluate 13a | 2nd Eluate 13b | 3rd Eluate 13b |
|---|---|---|---|
|  | N, 6.79. | N, 6.38. | N, 6.76. |

PREPARATION OF INTERMEDIATE 6-(1) (−)-(1R, 2S, 3S, 5S)-and (−)-(1R, 2R, 3S, 5S)-2-(benzenesulfonamido)-3-(2-propenyl)-6,6-dimethylbicyclo[3.1.1]heptanes 14c and 14d

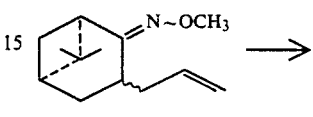

13a

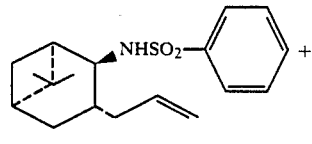

14c

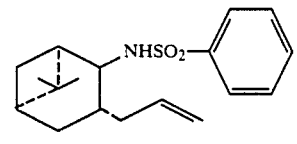

14d

To 160 ml of solution of 11.4 g of O-methyloxime 13a (prepared in 5) in 99% ethanol is added 14 g of sodium metal cut into small pieces in small portions over 3 hours under refluxing. The reaction mixture is refluxed with heating until sodium metal completely disappears, then cooled to room temperature and poured into water. The mixture is extracted with ether and the extract is washed with water, dried over anhydrous sodium sulfate and evaporated under reduced pressure.

A mixture of the residue, 10 ml benzenesulfonyl chloride, 26 ml of triethylamine and 165 ml of dichloromethane is allowed to stand at room temperature overnight and then poured into dilute hydrochloric acid under ice cooling. The organic layer is separated and the aqueous layer is extracted with dichloromethane. The combined extracts are washed with an aqueous solution of sodium hydrogencarbonate and water, dried over anhydrous sodium sulfate and evaporated under reduced pressure. The residue is purified by frash chromatography (300 g of silica gel, 230-400 mesh, eluted with hexane—ethyl acetate=4:1) to give two types of isomers 14c and 14d.

COMPOUND 14c

Yield 17.1%

$[\alpha]_D-32.0°$ (22° C., c 1.233, CHCl$_3$).

IR $\nu$ max(film): 3330, 1342, 1162 cm$^{-1}$.

NMR $\delta$ ppm(CDCl$_3$):0.93(3H,s), 1.04(3H,s), 0.7~2.8(9H, 3.95(1H,m), 4.82(1H,d,J=9 Hz), 4.90(1H,s), 5.00(1H,s), 5.11(1H,s), 5.75(1H,m), 7.4~7.6(3H,m), 7.7~8.0(2H,m).

COMPOUND 14d

Yield 75.5%
Mp. 93° C. (benzene)
$[\alpha]_D - 33.9°$ (22° C., c 1.144, CHCl$_3$).
IR $\nu$ max(Nujol): 3260, 1327, 1173 cm$^{-1}$.
NMR $\delta$ ppm(CDCl$_3$): 0.72(3H,s), 1.08(3H,s), 1.2-2.5(9H, .3.36(1H,t,J=8 Hz), 4.71(1)H,d,J=9 Hz), 4.89(1H,s), 5.03(1H,m), 5.70(1H,m), 7.4-7.7(3H,m), 7.8-8.0(2H,m).
Anal. Calcd. (%) for C$_{18}$H$_{25}$NO$_2$S,½(C$_6$H$_6$~H$_2$O): C 68.63, H 7.95, N 3.81, S 8.72. Found (%): C 68.53, H 7.61, N 3.95, S 8.89.

(2) Compound 13b is allowed to react in the same manner as in 6-(1) to give compound 14b.

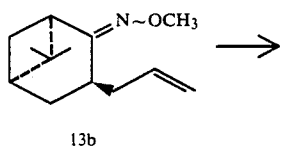

13b

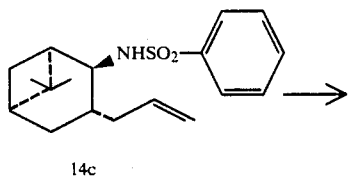

14b

Mp. 57°~58° C. (hexane).
$[\alpha]_D + 22.6°$ 22° C., c 1.353, CHCl$_3$).
IR $\nu$ max(Nujol): 3295, 1330, 1163 cm$^{-1}$.
NMR $\delta$ ppm(CDCl$_3$): 0.69(1H,d,J=10 Hz), 1.00(3H,s), 1.08(3H,s), 1.3~1.6(1H,m), 1.7~2.3(7H,m), 3.35(3H,m), 4.80(1H,dd,J=9.3 Hz), 4.96(1H,s), 5.14(1H,d,J=9 Hz), 5.4~5.9(1H,m), 7.4~7.6(3H,m), 7.8~8.2(2H,m).
Anal. Calcd. (%) for C$_{18}$H$_{25}$NO$_2$S: C 67.68, H 7.89, N 4.38, S 10.04. Found (%): C 67.44, H 7.94, N 4.43, S 9.85.

PREPARATION OF INTERMEDIATE 7. (−)-(1R, 2S, 3S, 5S)-2-Benzenesulfonamido-3-[(2RS)-2,3-epoxypropyl]-6,6-dimethylbicyclo[3.1.1]heptane 15c 14c 15c To a solution of 0.855 g of olefin 14c (prepared in 6) in 13 ml of dichloromethane is added 1.2 g of m-chloroperbenzoic acid in small portions under ice cooling. The reaction mixture is stirred at room temperature for 5 hours and insoluble material is filtered off and washed with dichloromethane. The filtrate is washed with an aqueous solution of sodium thiosulfate, an aqueous solution of sodium hydrogencarbonate and water, successively, dried over anhydrous sodium sulfate, and evaporated under reduced pressure. The residue is crystallized from benzene to give 0.95 g of the titled compound 15c.

Yield 95.5%.
Mp. 127°~131° C.
$[\alpha]_D - 34.7°$ (22° C., c 1.027, CHCl$_3$). NMR data indicate that compound 15c is a mixture of epimer.
IR $\nu$ max(Nujol): 3260, 1328, 1172 cm$^{-1}$.
NMR $\delta$ ppm(CDCl$_3$): 0.72(3H,s), 1.05, 1.07(total 3H,s), 1.3-2.2(9H), 2.38(1H,m), 2.72(1H,m), 2.86(1H,m), 3.331H,m), 4.80, 4.88(total 1H,d,J=8 Hz), 7.4~7.6(3H,m), 7.7~8.0(2H,m).
Anal. Calcd. (%) for C$_{21}$H$_{27}$NO$_3$S·½C$_6$H$_6$: C, 67.53; H, 7.28; N, 3.75; S, 8.58. Found (%): C, 67.13; H, 7.51; N, 3.85; S, 8.57.

PREPARATION OF INTERMEDIATE 8. (−)-(1R, 2S, 3S, 5S)-2-Benzenesulfonamido-6,6-dimethylbicyclo[3.1.1]hept-3-yl]acetoaldehyde 16c

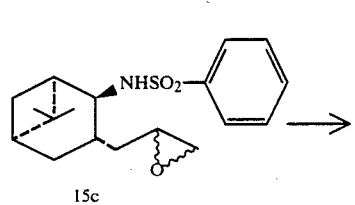

15c

16c

To a solution of 0.938 g of epoxide 15c (prepared in 7) in 10 ml of dioxane is dropwise added 3 ml of aqueous solution of 1.2 g of periodic acid at room temperature and the mixture is stirred at room temperature for 4 hours. The reaction mixture is washed with water, dried over anhydrous sodium sulfate, and evaporated under reduced pressure.

After the residue is purified by frash chromatography (silica gel, 230-400 mesh, eluted with hexane—ethyl acetate=3:2), the eluate is crystallized from hexane to give 445 mg of the titled compound 16c in 49.5% yield.
Mp. 108°-110° C.
IR: $\nu$ max(Nujol): 3215, 1704, 1328, 1151 cm$^{-1}$.
NMR $\delta$ ppm(CDCl$_3$): 0.70(3H,s), 1.06(3H,s), 1.3~2.9(9H), 3.33(1H,t,J=9 Hz), 4.87(1H,d,J=9 Hz), 7.4~7.6(3H,m), 7.7~7.9(2H,m), 9.70(1H,s).
Anal. Calcd. (%) for C$_{17}$H$_{23}$NO$_3$S: C, 63.52; H, 7.21; N, 4.36; S, 9.97. Found (%): C, 63.21; H, 7.23; N, 4.29; S, 9.73.

PREPARATION OF INTERMEDIATE 9. (−)-[(1R, 2R, 3R, 5S)-2-[2-Benzenesulfonamido-6,6-dimethylbicyclo[3.1.1]hept-3-yl]-acetoaldehyde 16b

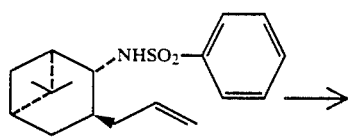
14b

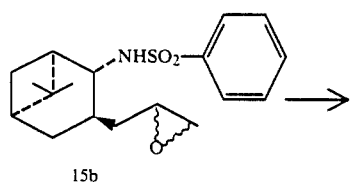
15b

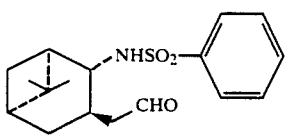
16b

Compound 14b [prepared in 6-(1)] is allowed to react in the same manner as in 7 to give compound 15b as an oil, which is allowed to react in the same manner as in 8 without further purification to give compound 16b.

COMPOUND 16b

NMR δ ppm(CDCl₃): 0.72(1H,d,J=10 Hz), 1.04(3H,s), 1.10(3H,s), 1.7~2.8(8H), 3.35(1H,dd,J=8,3 Hz), 3.69(3H,s), 5.17(1H,d,J=8 Hz), 7.4~7.7(3H,m), 7.80~8.0(2H,m), 9.62(1H,d,J=2 Hz).

EXAMPLE 16

(1) (−)-5(Z)-7-[(1R, 2R, 3R, 5S)-2-Benzenesulfonamido-6,6-dimethylbicyclo[3.1.1]hept-3-yl]-5-heptenoic acid 6d-a and its sodium salt 7d-a

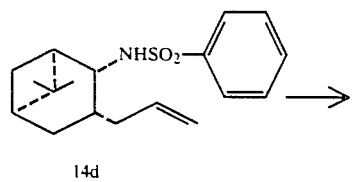
14d

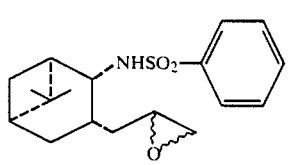
15d

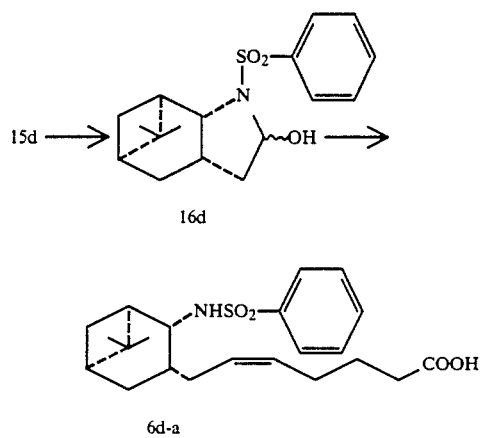

Compound 14d [prepared in 6-(1)] is allowed to react according to the manners of 7, 8, 1 and Example 8-(1) to give compound 6d-a as an oil.

COMPOUND 6d-a

[α]_D −4.7° (20° C., c 0.706, CH₃OH).
IR ν max(film): 3300, 1708, 1341, 1156 cm⁻¹.
NMR δ ppm(CDCl₃): 0.81(3H,s), 1.03(3H,s), 1.2~2.7(15H), 3.96(1H,m), 5.43(2H,m), 7.4~7.6(3H,m), 7.7~7.9(2H,m), 8.68(1H,br.s).

(2) Sodium salt 7d-a

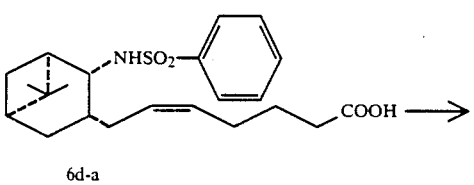
6d-a

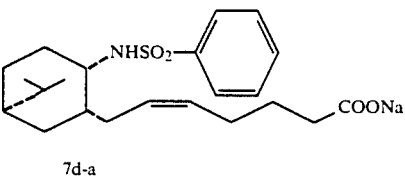
7d-a

Compound 6d-a is treated in the same manner as in Example 8-(2) to give sodium salt 7d-a.
IR ν max(KBr): 3290, 1565, 1322, 1159 cm⁻¹.

EXAMPLE 17

(1) (+)-5(E)-7-[(1R, 2R, 3S, 5S)-2-Benzenesulfonamido-6,6-dimethylbicyclo[3.1.1]hept-3-yl]-5-heptenoic acid 9b-a and its sodium salt 10b-a

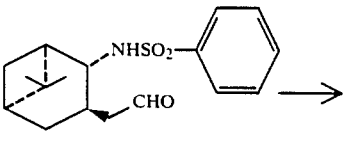
16b

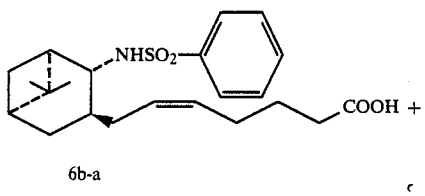

Compound 16b is treated in the same manner as in 1 and Example 8-(1) to give 6b-a and 9b-a.

COMPOUND 9b $[\alpha]_D + 26.5°$ (20° C., c 1.208, CH$_3$OH).
IR $\nu$ max(film): 3285, 1708, 1323, 1160 cm$^{-1}$.
NMR $\delta$ ppm(CDCl$_3$): 0.70(1H,d,J=8 Hz), 1.00(3H,s), 1.08(3H,s), 1.2~2.5(14H), 3.37(1H,m), 4.89(1H,d,J=8 Hz), 5.27(2H,m), 7.3~7.7(3H,m), 7.8~8.0(2H,m).

(2) Sodium salt 10b-a

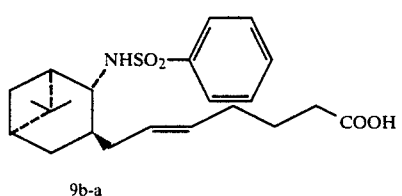

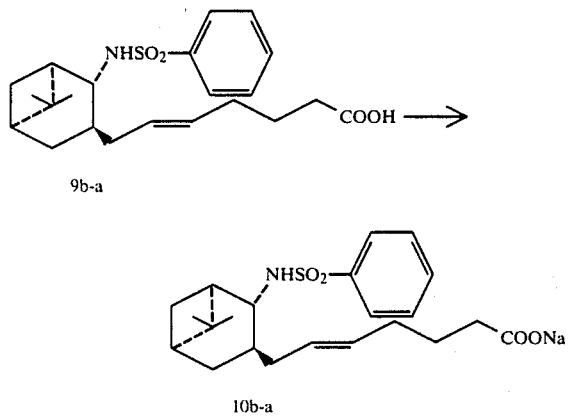

Compound 9b-a is treated in the same manner as in Example 8-(2) to give sodium salt 10b-a.

IR $\nu$ max(KBr): 3290, 1565, 1322, 1306, 1159, 967 cm$^{-1}$.

EXAMPLE 44 p-Methoxybenzylamine (+)-5(Z)-7-[(1R,2R,3S,4S)-2-benzenesulfonaminidobicyclo[3.1.1]hept-3-yl]-5-heptenoate 17b-a

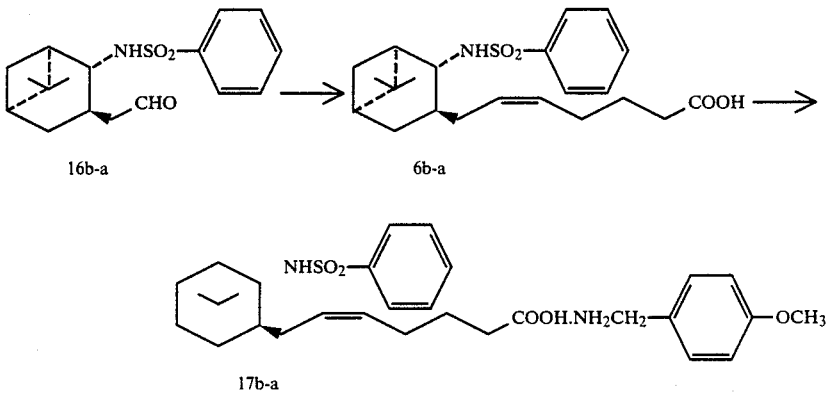

To a suspension of 36.46 g of (4-carboxybutyl)triphenylphosphonium bromide in 160 ml of dry tetrahydrofuran is added 18.46 g of potassium tert-butoxide under stirring in an nitrogen atmosphere and the mixture is stirred for 2 hours to prepare Wittig reagent. To the resulting mixture is slowly dropwise added a solution of 9.44 g of aldehyde 16b-a in 60 ml of tetrahydrofuran at 0° C. and the mixture is stirred at the same temperature for 2 hours. The reaction mixture added 200 ml of water is washed with 150 ml of ether twice. The aqueous layer is acidified to about pH 3 with 10% hydrochloric acid and then extracted with 200 ml of ether twice. The extract is washed successively, with water, an aqueous solution of sodium chloride, dried on anhydrous sodium sulfate, and evaporated under reduced pressure. To the resulting crude carboxylic acid dissolved in 40 ml of ethyl acetate is added 4.03 g of 4-methoxylbenzylamine in 10 ml of ethyl acetate and the mixture is allowed to stand at room temperature overnight and then filtrated to collect 10.9 g of the crystals which contain about 2% of E-olefin.

The crude salt (41.9 g) added 200 ml of 5% hydrochloric acid is extracted with ether. The extract is washed with water, dried, and evaporated to give the carboxylic acid which is treated with 4-methoxybenzylamine again to give 35.2 g of the titled compound 17b-a. The prepared compound is estimated to contain 0.6% of E-olefine by HPLC.

Mp. 125°~127° C.
$[\alpha]_D + 27.7$ (24° C., c 1.083, CH$_3$OH).
IR $\nu$ max(KBr): 1542, 1517, 1309, 1151 cm$^{-1}$.
NMR $\delta$ ppm(CDCl$_3$) 0.69(1H,d,J=9.8 Hz), 1.02(3H,s), 1.11(3H,s), 1.32~2.37(14H), 3.18(1H,m), 3.78(3H,s), 3.91(1H,d,J=13.8 Hz), 3.95(1H,d,J=13.8 Hz), 5.34(2H,m), 5.65(3H,br,s), 6.40(1H,br,s), 6.86(2H,d,J=8.7 Hz), 7.29(2H,d,J=8.7 Hz), 7.42~7.58(3H), 7.90(2H,m).
Anal. Calcd. (%) for C$_{30}$H$_{42}$N$_2$O$_5$S: C 66.39, H 7.80, N 5.16, S 5.91. Found (%): C 66.28, H 7.76, N 5.15, S 5.94.

The compounds of the present invention have a potent antagonistic action against the thromboxane A$_2$ receptor, and strongly inhibit platelet aggregation or vasoconstriction caused by thromboxane A₂. This means that the compounds of this invention are expected to be used as anti-thrombotic and anti-vasoconstricting drugs. The platelet aggregation inhibitory activity of the present invention is shown in the following in vitro test effected in the representative compounds of the present invention.

[MATERIAL TESTED AND METHOD]

From the abdominal artery of a male rat (Sprague-Dowley, 8 weeks old) was collected 10 ml of blood with a syringe containing 1.5 ml of ACD (85 mM sodium citrate, 70 mM citric acid, 110 mM glucose) and 20 μg of prostaglandin E₁. The blood is placed in a plastic test tube, mixed by moderate turning and centrifuged for 10 minutes at 160×g to give platelet rich plasma (PRP). To the prepared PRP was added apyrase (25 μg/ml) and the mixture was layered on 40% bovine serum albumin. The resulting mixture is centrifuged at 1200×g for 25 minutes. The platelet pellet suspended in a small amount of a buffer (137 mM NaCl, 2.7 mM KCl, 1.0 mM MgCl₂, 3.8 mM NaH₂PO₄, 3.8 mM Hepes, 5.6 mM glucose, 0.035% bovine serum albumin, pH 7.35) was applied on 10 ml of Sepharose 2B column and eluted with the buffer to prepare a washed platelet.

The platelet aggregation reaction was measured by an aggregometer (NKK HEMA TRACER 1 MODEL PAT-6A·6M, Niko bioscience). In a measuring cuvette was placed 245 μl of the washed platelet of which platelet number was adjusted to 5×10⁵/μl and set in the aggregometer. The washed platelet was stirred (1000 rpm) at 37° C. and 3.8 μl of 0.1M of CaCl₂ was added thereto. One minutes after, 0.5 μl of a solution of test compound (dimethylsulfoxide solution) was added and 2 minutes after, 1 μl of Collagen reagent Horm® [HORMON-CHEMIE München GMBH, final concentrate 4 μg/ml] as a platelet aggregating agent was added. The change in light transmittance caused by platelet aggregation was recorded against time elasped.

50% aggregation inhibitory rate was calculated from the aggregation inhibitory rate (which was measured 3 minutes after adding a platelet aggregating agent). The light transmittance for the washed platelet and the buffer were setted at 0% and 100%, respectively.

The results of the test are shown in Table 6.

TABLE 6

| Inhibition of Platelet Aggregation [50% Inhibitory Concentration (nM)] | |
|---|---|
| Test* Compound Number | Platelet Aggregating Agent Collagen |
| 7a-a | 11 |
| 7a-b | 115 |
| 7b-a | 0.7 |
| 7b-b | 1.7 |
| 7b-c | 3.7 |
| 7b-d | 5.3 |
| 7b-e | 6.4 |
| 7b-f | 1.3 |
| 7b-g | 9.9 |
| 7b-h | 26 |
| 7b-i | 3.4 |
| 7b-k | 1.8 |
| 7b-l | 9.9 |
| 7b-m | 4.3 |
| 7b-n | 480 |
| 7b-o | 240 |
| 7b-p | 13 |
| 7b-q | 12 |
| 10b-a | 1.4 |
| 7c-a | 233 |

TABLE 6-continued

| Inhibition of Platelet Aggregation [50% Inhibitory Concentration (nM)] | |
|---|---|
| Test* Compound Number | Platelet Aggregating Agent Collagen |
| 10c-a | 862 |
| 7d-a | 37 |
| 7e-a | 157 |
| 10e-a | 147 |
| ONO-11120 | 115 |

*Test compound number corresponds to that used in Example or the compound shown below.

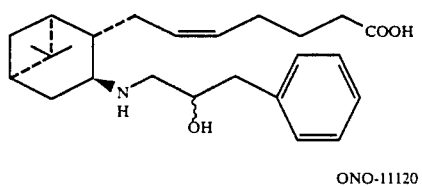

ONO-11120

The objective compounds of this invention show a potent inhibitory activity against platelet aggregation caused by collagen.

The objective compounds of the present invention strongly inhibit thromboxane induced platelet aggregation, vasoconstriction, and bronchoconstriction. Therefore, clinical application of such pharmacological action of the compound can be expected, that is, the compounds can be used for treatment or improvement of such symptoms as arteriosclerosis, myocardial infarction, acute ischemic angina pectoris, circulatory shock, sudden death and so forth. The objective compounds of the present invention can be administered orally or parenterally. For example, the compounds can be formulated into tablets, capsules, pills, granules, fine subtilaes, solutions, emulsions, suppositories, and injection for intravenous, intramusuclar, and subcutaneous administration. In preparing the pharmaceutical preparations of the compounds, adequate carriers and fillers are selected from conventionally used carriers and fillers.

The objective compounds of the present invention may be administered in a dose of about 10 to 800 mg per day for an adult.

What we claim is:

1. A compound of the formula:

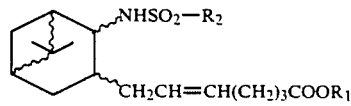

(wherein R₁ is hydrogen or lower alkyl; R₂ is lower alkyl, aralkyl or aryl which may be substituted by lower alkyl, alkoxy, acetoxy, hydroxy, halogen, nitro or phenyl; and the wavy line indicates R or S configuration or their mixture) or salt thereof.

2. A compound claimed in claim 1, wherein R₁ is phenyl which may be substituted by lower alkyl, alkoxy, acetoxy, hydroxy, halogen, nitro or phenyl.

3. A compound claimed in claim 1, namely, 5(Z)-7-[2-benzenesulfonamido-6,6-dimethylbicyclo[3.1.1]hept-3-yl]-5-heptenoic acid or salt thereof.

4. A compound claimed in claim 1, namely, 5(Z)-7-[6,6-dimethyl-2-(4-tosylamido)bicyclo[3.1.1]hept-3-yl]-5-heptenoic acid or salt thereof.

5. A compound claimed in claim 1, namele, 5(Z)-7-[2-(3-chlorobenzenesulfonamido)-6,6-dimethylbicyclo[3.1.1]hept-3-yl]-5-heptenoic acid or salt thereof.

6. A compound claimed in claim 1, namely, 5(Z)-7-[6,6-dimethyl-2-(4-hydroxybenzenesulfonamidobicyclo[3.1.1]hept-3-yl]-5-heptenoic acid or salt thereof.

7. A process for preparing a compound of the formula:

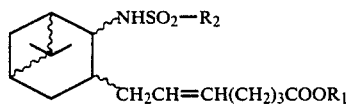

(wherein $R_1$ is hydrogen or lower alkyl; $R_2$ is lower alkyl, aralkyl or aryl which may be substituted by lower alkyl, alkoxy, acetoxy, hydroxy, halogen, nitro or phenyl; and the wavy line indicates R or S configuration or their mixture) or salt thereof which comprises reacting a compound of the formula:

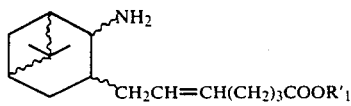

(wherein $R'_1$ is lower alkyl; and the wavy line is the same as defined above) or salt thereof with a compound of the formula: Hal—$SO_2$—$R_2$ (wherein Hal is halogen; and $R_2$ is the same as defined above) and, if necessary, applying the resulting compound to hydrolysis and/or salt formation.

8. A process for preparing a compound of the formula:

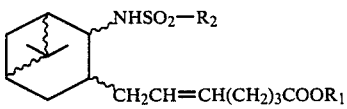

(wherein $R_1$ is hydrogen or lower alkyl; $R_2$ is lower alkyl, aralkyl or aryl which may be substituted by lower alkyl, alkoxy, acetoxy, hydroxy, halogen, nitro or phenyl; and the wavy line indicates R or S configuration or their mixture) or salt thereof which comprises reacting a compound of the formula:

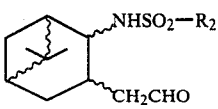

(wherein $R_2$ and the wavy line is the same as defined above) or its equivalent with a compound of the formual:

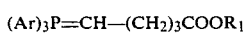

$(Ar)_3P=CH-(CH_2)_3COOR_1$ (wherein Ar is aryl; and $R_1$ is the same as defined above) and, if necessary, applying the resulting compound to esterfication, hydrolysis and/or salt formation.

* * * * *